(12) United States Patent
Ohtani et al.

(10) Patent No.: US 6,703,385 B1
(45) Date of Patent: Mar. 9, 2004

(54) TRICYCLIC COMPOUNDS HAVING SPLA$_2$-INHIBITORY ACTIVITIES

(75) Inventors: Mitsuaki Ohtani, Osaka (JP); Masahiro Fuji, Osaka (JP); Makoto Adachi, Osaka (JP); Tomoyuki Ogawa, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 55 days.

(21) Appl. No.: 10/031,443

(22) PCT Filed: Jul. 14, 2000

(86) PCT No.: PCT/JP00/04722

§ 371 (c)(1),
(2), (4) Date: Jan. 22, 2002

(87) PCT Pub. No.: WO01/05789

PCT Pub. Date: Jan. 25, 2001

(30) Foreign Application Priority Data

Jul. 19, 1999 (JP) ............................................. 11-204338
Feb. 24, 2000 (JP) ........................................... 2000-47074

(51) Int. Cl.$^7$ ...................... A61K 31/33; A61K 31/495;
C07D 24/36; C07D 487/00; C07D 498/00
(52) U.S. Cl. ........................ 514/183; 514/248; 514/256;
544/338; 544/344; 544/380
(58) Field of Search ................................ 514/183, 248,
514/250; 544/338, 344, 380

(56) References Cited

FOREIGN PATENT DOCUMENTS

| EP | 0 620 214 A1 | 10/1994 |
|----|---|---|
| EP | 0 620 215 A1 | 10/1994 |
| EP | 0 675 110 A1 | 10/1995 |
| EP | 1 085 021 A1 | 3/2001 |
| JP | 56-030979 A2 | 3/1981 |
| JP | 03-099082 A2 | 4/1991 |
| JP | 04-270288 A2 | 9/1992 |
| WO | WO 96/03120 A1 | 2/1996 |
| WO | WO 96/03376 A1 | 2/1996 |
| WO | 9603383 * | 2/1996 |
| WO | WO 96/03383 A1 | 2/1996 |
| WO | WO 97/21664 A1 | 6/1997 |
| WO | WO 97/21716 A1 | 6/1997 |
| WO | WO 98/18464 A1 | 5/1998 |
| WO | WO 98/24437 A1 | 6/1998 |
| WO | WO 98/24756 A1 | 6/1998 |
| WO | WO 98/24794 A1 | 6/1998 |
| WO | WO 98/25609 A1 | 6/1998 |
| WO | WO 99/51605 A1 | 10/1999 |

OTHER PUBLICATIONS

Granata et al (PubMed 12876405, also cited as Int.Arch. Allergy Immunol. 131/3,153–63(2003).*

Scott et al(PubMed Abstract 12783578, also cited as Expert Opin. Ther. Targets, 7/3,427–40(2003).*

Hagishita et al., "Potent Inhibitors of Secretory Phospholipase A2:Synthesis and Inhibitory Activities of Indolizine and Indene Derivatives", *J. Med. Chem.,* (1996), pp. 3636–3658, vol. 39, American Chemical Society, USA.

Kakehi et al., "Preparation of New Nitrogen–Bridged Heterocycles. 19.$^1$) Smooth Syntheses of Thieno[3,2–a]–and Thieno[2,3–b]indolizine Derivatives", *Bull. Chem. Soc. Jpn.,* Jan. 1989, pp. 119–127, vol. 62, The Chemical Society of Japan, Japan.

Reynolds et al.,"Analysis of Human Synovial Fluid Phospholipase A$_2$ on Short Chain Phosphatidylcholine–Mixed Micelles: Development of a Spectrophotometric Assay Suitable for a Microtiterplate Reader", *Analytical Biochemistry,* (1992), pp. 190–197, vol. 204, Academic Press, Inc., USA .

Kanda et al., "Characterization of recombinant human and rat pancreatic phospholipases A$_2$ secreted from *Saccharomyces cerevisiae*; difference in proteolytic processing", *Biochimica et Biophysica Acta,* (1992), pp. 1–10, Elsevier Science Publishers B.V., USA.

Chen et al., "Cloning and Recombinant Expression of a Novel Human Low Molecular Weight Ca$^{2+}$–dependent Phospholipase A$_2$", *The Journal of Biological Chemistry,* Jan. 28, 1994, pp. 2365–2368, vol. 269, No. 4, The American Society for Biochemistry and Molecular Biology, Inc., USA.

(List continued on next page.)

Primary Examiner—Richard L. Raymond
Assistant Examiner—Sudhaker B. Patel
(74) Attorney, Agent, or Firm—Foley & Lardner

(57) ABSTRACT

The present invention provides a compound having sPLA$_2$ inhibiting activity.

The compound represented by the formula (I):

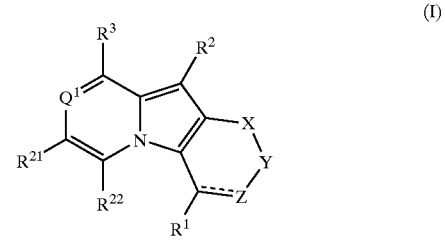

(I)

wherein R$^1$ is (a) C1 to C20 alkyl, C2 to C20 alkenyl, C2 to C20 alkynyl, carbocyclic groups, heterocyclic groups or the like; R$^2$ is COCONH$_2$ or the like; Q$^1$ is a nitrogen atom or C—R$^4$; one of R$^3$ and R$^4$ is —(L$^2$)-(acidic group) wherein L$^2$ is a group connecting with an acid group and the length of the connecting groups 1 to 5 atoms, and the other is a hydrogen atom; R$^{21}$ and R$^{22}$ are hydrogen atoms or the like; X is —CR$^{23}$R$^{24}$— or the like wherein R$^{23}$ and R$^{24}$ are hydrogen atoms or the like; Y is —CR$^{25}$R$^{26}$— or the like wherein R$^{25}$ and R$^{26}$ are hydrogen atoms or the like; Z is CH$_2$ or the like; a broken line ( - - - ) represents the presence or absence of a bond, its prodrug, their pharmaceutically acceptable salt, or solvate thereof.

12 Claims, No Drawings

OTHER PUBLICATIONS

Cupillard et al., "Cloning, Chromosomal Mapping, and Expression of a Novel Human Secretory Phospholipase $A_2$", *The Journal of Biological Chemistry,* Jun. 20, 1997, pp. 15745–15752, vol. 272, No. 25, The American Society for Biochemistry and Molecular Biology, Inc., USA.

* cited by examiner

TRICYCLIC COMPOUNDS HAVING SPLA$_2$-INHIBITORY ACTIVITIES

TECHNICAL FIELD

The present invention relates to a tricyclic compound effective for inhibiting sPLA$_2$-mediated fatty acid release.

BACKGROUND ART sPLA$_2$ (secretory phospholipase A$_2$) is an enzyme that hydrolyzes membrane phospholipids and has been considered to be a rate-determining enzyme that governs the so-called arachidonate cascade where arachidonic acid, the hydrolysis product, is the starting material. Moreover, lysophospholipids that are produced as by-products in the hydrolysis of phospholipids have been known as important mediators in cardiovascular diseases. Accordingly, in order to normalize excess functions of the arachidonate cascade and the lysophospholipids, it is important to develop compounds which inhibit the liberation of sPLA$_2$-mediated fatty acids (for example, arachidonic acid), namely, compounds which inhibit the activity or production of sPLA$_2$. Such compounds are useful for general treatment of symptoms, which are induced and/or sustained by an excess formation of sPLA$_2$, such as septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, cardiac infarction, and so on. The participation of sPLA$_2$ is considered to be extremely wide and, besides, its action is potent.

Examples of sPLA$_2$ inhibitors include compounds described in EP-620214 (JP Laid-Open No. 010838/95, U.S. Pat. No. 5,578,634), EP-620215 (JP Laid-Open No. 025850/95, U.S. Pat. No. 5,684,034), EP-675110 (JP Laid-Open No. 285933/95, U.S. Pat. No. 5,654,326), WO 96/03120 (JP Laid-Open No. 505336/98), WO 96/03376 (JP Laid-Open No. 503208/98, U.S. Pat. No. 5,641,800), WO 96/03383 (JP Laid-Open No. 505584/98), WO 97/21664 (EP-779271), WO 97/21716 (EP-779273), WO 98/18464 (EP839806), WO98/24437(EP846687), WO98/24756, WO98/24794, WO98/25609, WO99/51605, WO99/59999 and the like, or parabromophenacylbromide, mepacrine, manoaride, theilocien A and the like.

DISCLOSURE OF INVENTION

The object of the present invention is to provide tricyclic compounds having sPLA$_2$ inhibitory activity and being useful for treatment or prevention of inflammatory diseases.

The present invention relates to I) a compound represented by the formula (I):

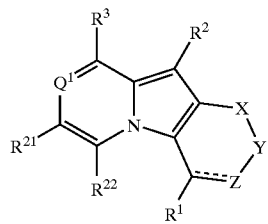

(I)

wherein R$^1$ is (a) C1 to C20 alkyl, C2 to C20 alkenyl, C2 to C20 alkynyl, carbocyclic groups, and heterocyclic groups, (b) the groups represented by (a) each substituted independently with at least one group selected from non-interfering substituents, or (c) —(L$^1$)—R$^5$ wherein L$^1$ is a divalent linking group of 1 to 18 atom(s) selected from hydrogen atom(s), nitrogen atom(s), carbon atom(s), oxygen atom(s), and sulfur atom(s), and R$^5$ is a group selected from the groups (a) and (b);

R$^2$ is a group represented by the formula:

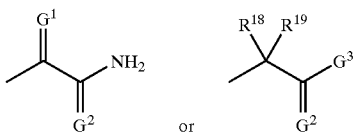

wherein R$^{18}$ and R$^{19}$ are independently a hydrogen atom, C1 to C3 alkyl or a halogen; G$^1$ and G$^2$ are independently an oxygen atom or a sulfur atom; and G$^3$ is —NH$_2$ or —NHNH$_2$;

Q$^1$ is a nitrogen atom or C—R$^4$;

one of R$^3$ and R$^4$ is —(L$^2$)-(acidic group) wherein L$^2$ is an acid linker having an acid linker length of 1 to 5 and the other is a hydrogen atom, provided that when Q$^1$ is nitrogen, R$^3$ is —(L$^2$)-(acidic group) wherein L$^2$ and acidic group are as defined above;

R$^{21}$ and R$^{22}$ are independently a hydrogen atom, C1 to C6 alkyl, aryl, a halogen or aralkyl;

X is —CR$^{23}$R$^{24}$—, O, or S, wherein R$^{23}$ and R$^{24}$ are independently a hydrogen atom or C1 to C6 alkyl;

Y is a bond or —CR$^{25}$R$^{26}$—, wherein R$^{25}$ and R$^{26}$ are independently a hydrogen atom or C1 to C6 alkyl;

Z is CHR$^A$, CR$^A$, N, or NR$^B$—, wherein R$^A$ is a hydrogen atom, alkyloxycarbonyl, or carboxy; R$^B$ is a hydrogen atom or acyl;

a broken line ( - - - ) represents the presence or absence of a bond, its prodrug, their pharmaceutically acceptable salt, or solvate thereof.

In more detail, the present invention relates to II)-XIV).

II) A compound represented by the formula (II):

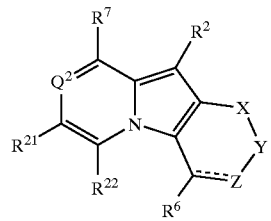

(II)

wherein R$^2$, R$^{21}$, R$^{22}$, X, Y, Z, and - - - are as defined above;

R$^6$ is —(CH$_2$)$_m$—R$^9$ wherein m is an integer from 0 to 6, and R$^9$ is (d) a group represented by the formula:

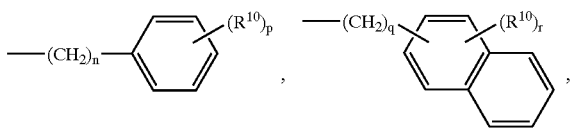

-continued

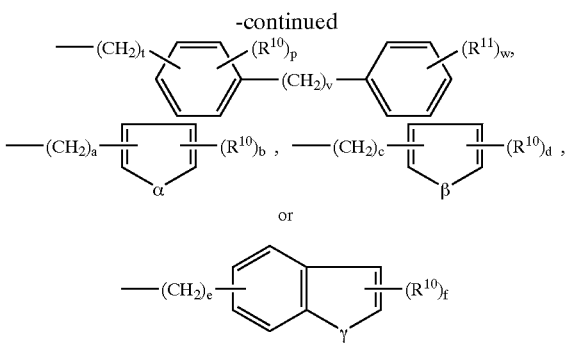

wherein a, c, e, n, q, t and v are independently an integer from 0 to 2; $R^{10}$ and $R^{11}$ are independently selected from a halogen, C1 to C10 alkyl, C1 to C10 alkyloxy, C1 to C10 alkylthio, optionally substituted phenyl, and C1 to C10 haloalkyl; α is an oxygen atom or a sulfur atom; β is —CH$_2$— or —(CH$_2$)$_2$—; γ is an oxygen atom or a sulfur atom; b is an integer from 0 to 3; d is an integer from 0 to 5; f, p, and w are independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen; $Q^2$ is a nitrogen atom or C—$R^8$; one of $R^7$ and $R^8$ is —(L$^3$)—$R^{12}$ wherein L$^3$ is represented by the formula:

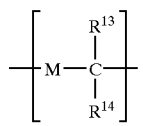

wherein M is —CH$_2$—, —O—, —N(R$^{15}$)—, or —S—; $R^{13}$ and $R^{14}$ are independently a hydrogen atom, C1 to C10 alkyl, aryl, aralkyl, carboxy, or a halogen, and $R^{15}$ is C1 to C6 alkyl; and $R^{12}$ is represented by the formula:

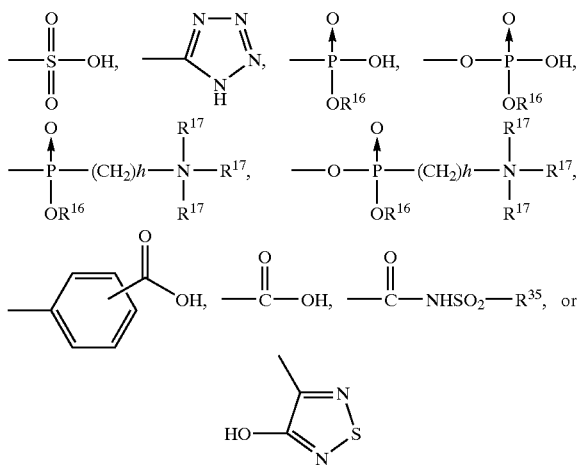

wherein $R^{16}$ is a hydrogen atom, a metal, or C1 to C10 alkyl, $R^{17}$ is independently a hydrogen atom or C1 to C10 alkyl; $R^{35}$ is C1–C5 alkyl or phenyl; h is an integer from 1 to 8; and the other is hydrogen atom;

provided that $R^7$ is —(L$^3$)—$R^{12}$, wherein L$^3$ and $R^{12}$ are as defined above, when $Q^2$ is a nitrogen atom, its prodrug, their pharmaceutically acceptable salt, or solvate thereof.

When the above b, d, f, p, r, u, and/or w are 2 or more, a plural number of $R^{10}$ or $R^{11}$ may be different from one another. When $R^{10}$ is a substituent on the naphthyl group, the substituent may be substituted at any arbitrary position on the naphthyl group.

—CH$_2$— and —(CH$_2$)$_2$— in β may be substituted with $R^{10}$.

III) A compound, its prodrug, their pharmaceutically acceptable salt, or solvate thereof as described in above I) or II), wherein said $R^1$ and $R^6$ are represented by the formula:

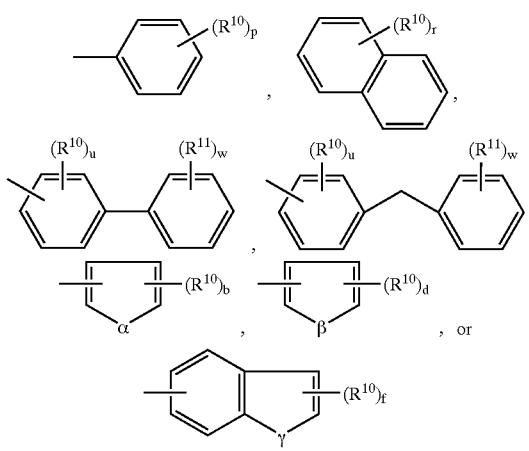

wherein $R^{10}$, $R^{11}$, b, d, f, p, r, u, w, α, β, and γ are as defined above.

When the above b, d, f, p, r, u, and/or w are 2 or more, a plural number of $R^{10}$ or $R^{11}$ may be different from one another. When $R^{10}$ is a substituent on the naphthyl group, the substituent may be substituted at any arbitrary position on the naphthyl group.

—CH$_2$— and —(CH$_2$)$_2$— in β may be substituted with $R^{10}$.

IV) A compound, its prodrug, their pharmaceutically acceptable salt, or solvate thereof as described in any one of I) to III), wherein said $R^1$ and $R^6$ are represented by the formula:

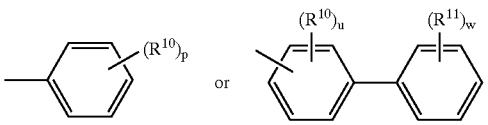

wherein $R^{10}$, $R^{11}$, p, u, and w are as defined above.

When the above p, u, and/or w are 2 or more, a plural number of $R^{10}$ or $R^{11}$ may be different from one another.

V) A compound, its prodrug, their pharmaceutically acceptable salt, or solvate thereof as described in any one of I) to IV), wherein said $R^3$ and $R^7$ are —O—(CH$_2$)$_g$—COOH (g is an integer from 1 to 6).

VI) A compound, its prodrug, their pharmaceutically acceptable salt, or solvate thereof as described in any one of I) to V), wherein said $R^2$ is —COCONH$_2$.

VII) A compound, its prodrug, their pharmaceutically acceptable salt, or solvate thereof as described in any one of I) to VI), wherein said both $R^{21}$ and $R^{22}$ are hydrogen atoms.

VIII) A compound represented by the formula (III):

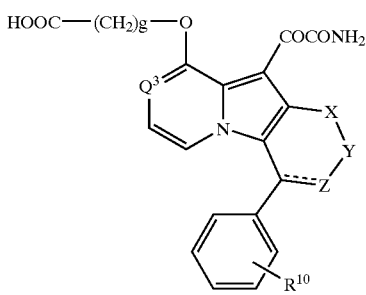

(III)

wherein $R^{10}$, X, Y, Z, g, and - - - are as defined above, $Q^3$ is a nitrogen atom, or CH,
its prodrug, their pharmaceutically acceptable salt, or solvate thereof.

IX) A compound, its prodrug, their pharmaceutically acceptable salt, or solvate thereof as described in any one of I) to VIII), wherein said (X, Y, Z) is ($CH_2$, $CH_2$, CH), ($CH_2$, $CH_2$, $CH_2$), ($CH_2$, $CH_2$, $NR^B$), (S, single bond, $CR^A$), or (S, single bond, CH), wherein $R^A$ and $R^B$ are as defined above.

X) A pharmaceutical composition containing a compound as described in any one of I) to IX) as an active ingredient.

XI) A pharmaceutical composition as described in X), which is for inhibiting $sPLA_2$.

XII) A pharmaceutical composition as described in X), which is for treatment or prevention of inflammatory diseases.

XIII) Use of a compound of any one of I) to IX) for preparation of a pharmaceutical composition for treating inflammatory diseases.

XIV) A method for treating a mammal, including a human, to alleviate the pathological effects of inflammatory diseases, which comprises administration to said mammal of a compound as described in any one of I) to IX) in a pharmaceutically effective amount.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes (f) cycloalkyl (such as cyclopropyl, cyclobutyl, cyclopentyl, cyclohexyl, cycloheptyl, and cyclooctyl); cycloalkenyl (such as cyclobutylenyl, cyclopentenyl, cyclohexenyl, cycloheptenyl, and cyclooctenyl); phenyl, naphthyl, norbornyl, bicycloheptadienyl, indenyl, stilbenyl, terphenylyl, phenylcyclohexenyl, acenaphthyl, anthoryl, biphenylyl, bibenzylyl, and a phenylalkylphenyl derivative represented by the formula:

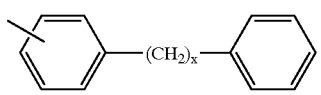

(V)

wherein x is an integer from 1 to 8.

The term "heterocyclic group" used in the present specification means a group derived from monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl and the like.

Preferred carbocyclic and heterocyclic groups in $R^1$ are (g) a group represented by the formula:

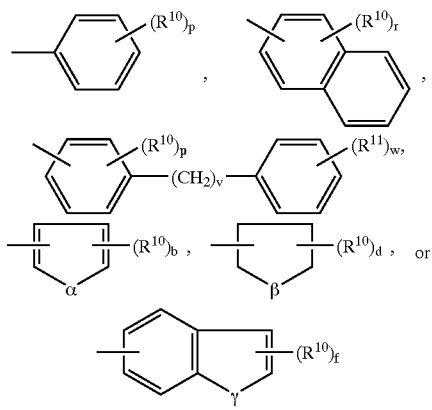

wherein v is an integer from 0 to 2; $R^{10}$ and $R^{11}$ are independently selected from a halogen, C1 to C10 alkyl, C1 to C10 alkyloxy, C1 to C10 alkylthio, optionally substituted phenyl, and C1 to C10 haloalkyl, α is an oxygen atom or a sulfur atom, β is —$CH_2$— or —$(CH_2)_2$—; γ is an oxygen atom or a sulfur atom; b is an integer from 0 to 3, d is an integer from 0 to 4; f, p, and w are an integer from 0 to 5; r is an integer from 0 to 7, and u is an integer from 0 to 4. When the above b, d, f, p, r, u, and/or w are 2 or more, a plural number of $R^{10}$ or $R^{11}$ may be different from one another. When $R^{10}$ is a substituent on the naphthyl group, the substituent may be substituted at any arbitrary position on the naphthyl group. —CH$_2$— and —(CH$_2$)$_2$— in β may be substituted with R$^{10}$.

A more preferable example includes (h) a group represented by the formula:

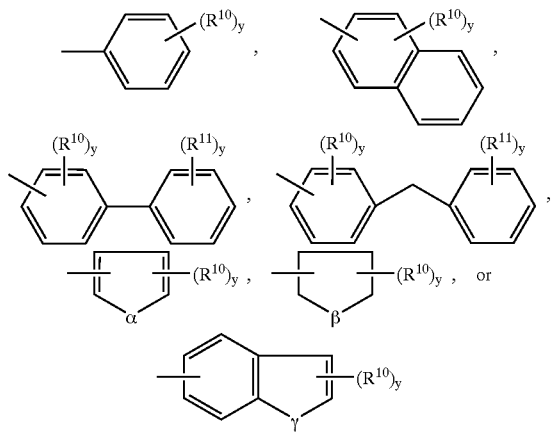

wherein R$^{10}$, R$^{11}$, α, β, and γ are the same as defined above, and y is 0 or 1. When R$^{10}$ is a substituent on the naphthyl group, the substituent may be substituted at any arbitrary position on the naphthyl group. —CH$_2$— and —(CH$_2$)$_2$— in β may be substituted with R$^{10}$.

The term "non-interfering substituent" in the present specification means a group suitable for substitution of group (a) (e.g., "alkyl", "alkenyl" "carbocyclic group" and "heterocyclic group") in R$^1$ on tricyclic compound represented by the formula (I). An example of the non-interfering substituents includes C1 to C10 alkyl, C2 to C6 alkenyl, C2 to C6 alkynyl, C7 to C12 aralkyl (such as benzyl and phenethyl), C7 to C12 alkaryl, C3 to C8 cycloalkyl, C3 to C8 cycloalkenyl, phenyl, tolyl, xylyl, biphenylyl, C1 to C10 alkyloxy, C1 to C6 alkyloxy C1 to C6 alkyl (such as methyloxymethyl, ethyloxymethyl, methyloxyethyl, and ethyloxyethyl), C1 to C6 alkyloxy C1 to C6 alkyloxy (such as methyloxymethyloxy and methyloxyethyloxy), C1 to C6 alkylcarbonyl (such as methylcarbonyl and ethylcarbonyl), C1 to C6 alkylcarbonylamino (such as methylcarbonylamino and ethylcarbonylamino), C1 to C6 alkyloxyamino (such as methyloxyamino and ethyloxyamino), C1 to C6 alkyloxyaminocarbonyl (such as methyloxyaminocarbonyl and ethyloxyaminocarbonyl), mono or di C1 to C6 alkylamino (such as methylamino, ethylamino, dimethylamino, and ethylmethylamino), C1 to C10 alkylthio, C1 to C6 alkylthiocarbonyl (such as methylthiocarbonyl and ethylthiocarbonyl), C1 to C6 alkylsulfinyl (such as methylsulfinyl and ethylsulfinyl), C1 to C6 alkylsulfonyl (such as methylsulfonyl and ethylsulfonyl), C2 to C6 haloalkyloxy (such as 2-chloroethyloxy and 2-bromoethyloxy), C1 to C6 haloalkylsulfonyl (such as chloromethylsulfonyl and bromomethylsulfonyl), C1 to C10 haloalkyl, C1 to C6 hydroxyalkyl (such as hydroxymethyl and hydroxyethyl), C1–C6 alkyloxycarbonyl (such as methyloxycarbonyl and ethyloxycarbonyl), —(CH$_2$)z-O—(C1 to C6 alkyl), benzyloxy, aryloxy (such as phenyloxy), arylthio (such as phenylthio), —(CONHSO$_2$R$^{20}$), formyl, amino, amidino, halogen, carbamyl, carboxyl, carbalkyloxy, —(CH$_2$)z-COOH (such as carboxymethyl, carboxyethyl, and carboxypropyl), cyano, cyanoguanidino, guanidino, hydrazido, hydrazino, hydroxy, hydroxyamino, nitro, phosphono, —SO$_3$H, thioacetal, thiocarbonyl, carbonyl, carbocyclic groups, heterocyclic groups and the like, wherein z is an integer from 1 to 8 and R$^{20}$ is C1 to C6 alkyl or aryl.

Preferable are halogens, C1 to C6 alkyl, C1 to C6 alkyloxy, C1 to C6 alkylthio, and C1 to C6 haloalkyl as the "non-interfering substituent" in the R$^1$. More preferable are halogens, C1 to C3 alkyl, C1 to C3 alkyloxy, C1 to C3 alkylthio, and C1 to C3 haloalkyl.

These groups may be substituted by at least one substituent selected from the group consisting of C1 to C6 alkyl, C1 to C6 alkyloxy, C2 to C6 haloalkyloxy, C1 to C6 haloalkyl, and halogens.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a tricyclic nucleus through a suitable linking atom (hereinafter defined as "acid linker"). An example of the acidic group includes (k) a group represented by the formula:

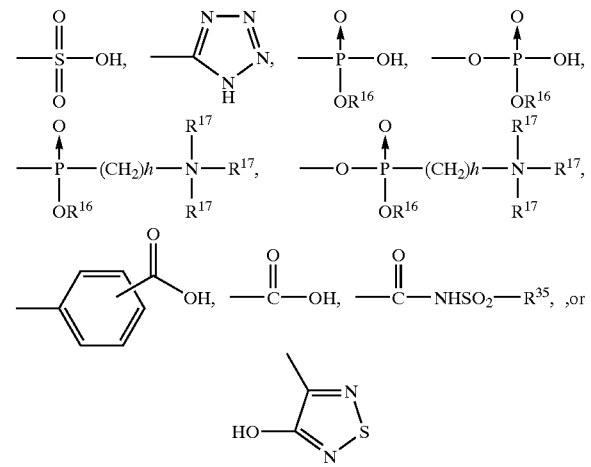

wherein R$^{16}$ is a hydrogen atom, a metal, or C1 to C10 alkyl; each R$^{17}$ is independently a hydrogen atom or C1 to C10 alkyl; R35 is C1–C5 alkyl or phenyl; h is an integer from 1 to 8. Preferable is (1) —COOH, —SO$_3$H, or P(O)(OH)$_2$. More preferable is (m) —COOH. And preferable is also their ester and prodrug.

The term "acid linker" in the present specification means a divalent linking group represented by a symbol —(L$^2$)—, and it functions to join tricyclic nucleus to an "acidic group" in the general relationship. An example of it includes (n) a group represented by the formula:

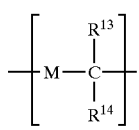

wherein M is —CH$_2$—, —O—, —N(R$^{15}$)—, or —S—, and R$^{13}$ and R$^{14}$ are independently a hydrogen atom, C1 to C10 alkyl, aryl, aralkyl, carboxy, or halogens, wherein R15 is C1–C6 alkyl and Ph is phenyl. Preferable are (o) —O—CH$_2$—, —S—CH$_2$—, —N(R$^{15}$)—CH$_2$—, —CH$_2$—CH$_2$—, —O—CH(CH$_3$)—, or —O—CH((CH$_2$)$_2$Ph)— wherein R$^{15}$ is C1 to C6 alkyl and Ph is phenyl. More preferable is (p) —O—CH$_2$— or —S—CH$_2$—.

In the present specification, the term "acid linker length" means the number of atoms (except for hydrogen atoms) in the shortest chain of a linking group —(L$^2$)— which connects tricyclic nucleus with the "acidic group". The presence of a carbocyclic ring in —(L$^2$)— counts as the number of atoms approximately equivalent to the calculated diameter of the carbocyclic ring. Thus, a benzene and cyclohexane ring in the acid linker counts as two atoms in culculating the length of —(L$^2$)—. A preferable length is 2 to 3.

The term "haloalkyl" in the present specification means the aforementioned "alkyl" substituted with the aforementioned "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred.

The term "aralkyl" in the present specification means a group wherein the aforementioned "alkyl" is substituted with the above-mentioned "aryl". Such aryl may have a bond at any substitutable position. An example of it includes benzyl, phenethyl, phenylpropyl (such as 3-phenylpropyl), naphthylmethyl (such as 1-naphthylmethyl) and the like.

The term "alkyloxycarbonyl" in the present specification means C1–C6 alkyloxycarbonyl. An example of the alkyloxycarbonyl includes methyloxycarbonyl, ethyloxycarbonyl, n-propyloxycarbonyl and the like.

The term "acyl" in the present specification means C1–C6 alkylcarbonyl or arylcarbonyl opptionally substituted with a halogen and the like. An example of the acyl includes acetyl, trifluoroacetyl, propionyl, benzoyl and the like.

A group of preferable substituents as the R$^1$ to R$^4$ and the X to Z of the compound represented by the formula (I) will be shown in items (A) to (W). Preferable are hydrogen atoms as both the R$^{21}$ and the R$^{22}$. Items (f) to (p) are the same group as described above.

As the R$^1$, (A):—(L$^1$)—R$^9$, (B):—(CH$_2$)$_{1-2}$-(f), (C):—(CH$_2$)$_{1-2}$-(g), and (D):—(CH$_2$)$_{1-2}$-(h) are preferred.

As the R$^2$, (E):—COCONH$_2$, —CH$_2$CONH$_2$, or —CH$_2$CO NHNH$_2$, and (F):—COCONH$_2$ are preferred.

As the R$^3$, (G):-(n)-(k), (H):-(n)-(l), (I):-(n)-(m), (J):-(o)-(k), (K):-(o)-(l), (L):-(o)-(m), (M):-(p)-(k), (N):-(p)-(l), and (O):-(p)-(m) are preferred.

As the R$^4$, (P): a hydrogen is preferred.

As the (X,Y,Z) preferable are as the (X,Y,Z), (Q):(CH$_2$,CH$_2$,CH), (CH$_2$,CH$_2$,CH$_2$), (CH$_2$,CH$_2$,NR$^B$), (S, a single bond, CR$^A$), and (S, a single bond, CH), wherein R$^A$ and R$^B$ are the same as described above.

A preferred group of compounds represented by the formula (I) is shown below.

That is, compounds represented by the formula (I-A):

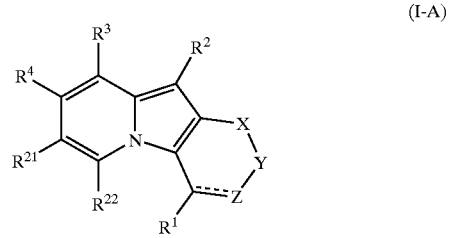

(R$^1$,R$^2$,R$^3$,R$^4$,(X,Y,Z))=(A,E,G,P,Q),(A,E,H,P,Q),(A,E,I,P,Q),(A,E,J,P,Q), (A,E,K,P,Q),(A,E,L,P,Q),(A,E,M,P,Q),(A,E,N,P,Q),(A,E,O,P,Q),(A,F,G,P,Q), (A,F,H,P,Q),(A,F,I,P,Q),(A,F,J,P,Q),(A,F,K,P,Q),(A,F,L,P,Q),(A,F,M,P,Q), (A,F,P,Q), (B,E,L,P,Q),(B,E,M,P,Q),(B,E,N,P,Q),(B,E,O,P,Q),(B,F,G,P,Q),(B,F,H,P,Q), (B,F,I,P,Q),(B,F,J,P,Q),(B,F,K,P,Q),(B,F,L,P,Q),(B,F,M,P,Q),(B,F,N,P,Q), (B,F,O,P,Q),(C,E,G,P,Q), (C,E,H,P,Q),(C,E,H,P,Q),(C,E,J,P,Q),(C,E,K,P,Q), (C,E,L,P,Q),(C,E,M,P,Q),(C,E,N,P,Q),(C,E,O,P,Q),(C,F,G,P,Q),(C,F,H,P,Q), (C,F,I,P,Q),(C,F,J,P,Q),(C,F,K,P,Q),(C,F,L,P,Q),(C,F,M,P,Q),(C,F,N,P,Q), (C,F,O,P,Q),(D,E,G,P,Q),(D,E,H,P,Q),(D,E,I,P,Q),(D,E,J,P,Q),(D,E,K,P,Q), (D,E,L,P,Q),(D,E,M,P,Q),(D,E,N,P,Q),(D,E,O,P,Q),(D,F,G,P,Q),(D,F,H,P,Q), (D,F,I,P,Q),(D,F,J,P,Q),(D,F,K,P,Q),(D,F,L,P,Q),(D,F,M,P,Q),(D,F,N,P,Q), and (D,F,O,P,Q)

compounds represented by the formula (I-B):

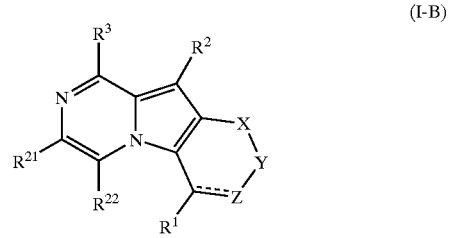

R$^1$,R$^2$,R$^3$,(X,Y,Z))=(A,E,G,Q),(A,E,H,Q),(A,E,I,Q), (A,E,J,Q),(A,E,K,Q),(A,E,L,Q),(A,E,M,Q),(A,E,N,Q),(A,E,O,Q), (A,F,G,Q),(A,F,H,Q), (A,F,I,Q),(A,F,J,Q),(A,F,K,Q),(A,F,L,Q),(A,F,M,Q),(A,F,N,Q),(A,F,O,Q),(B,E,G,Q), (B,E,H,Q),(B,E,I,Q),(B,E,J,Q),(B,E,K,Q),(B,E,L,Q),(B,E,M,Q),(B,E,N,Q),(B,E,O,Q), (B,F,G,Q),(B,F,H,Q),(B,F,I,Q),(B,F,J,Q),(B,F,K,Q),(B,F,L,Q),(B,F,M,Q), (B,F,N,Q),(B,F,O,Q),(C,E,G,Q),(C,E,H,Q),(C,E,I,Q),(C,E,J,Q),(C,E,K,Q), (C,E,L,Q), (C,E,M,Q),(C,E,N,Q),(C,E,O,Q),(C,F,G,Q),(C,F,H,Q),(C,F,I,Q), (C,F,J,Q),(C,F,K,Q),(C,F,L,Q),(C,F,M,Q),(C,F,N,Q), (C,F,O,Q),(D,E,G,Q),(D,E, H,Q), (D,E,I,Q),(D,E,J,Q),(D,E,K,Q),(D,E,L,Q),(D,E,M,Q),(D,E,N,Q),(D,E,O,Q), (D,F,G,Q),(D,F,H,Q),(D,F,I,Q),(D,F,J,Q),(D,F,K,Q),(D,F,L,Q),(D,F,M,Q), (D,F,N,Q), and (D,F,O,Q).

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, chronic rheumatism, arterial sclerosis, cereberal hemorrhage, cerebral infarction, cardiac failure, cardiac infarction, psoriasis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathrics, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

The term "solvate" includes, for example, solvates with organic solvents, hydrates, and the like. In case of forming a hydrate, a questioned compound may be coordinated with a suitable number of water molecules.

BEST MODE FOR CARRYING OUT THE INVENTION

The compounds of the invention represented by the formula (I) can be synthesized in accordance with well-known method described in chemical journals. The compounds can also be synthesized in accordance with following the methods A to E.

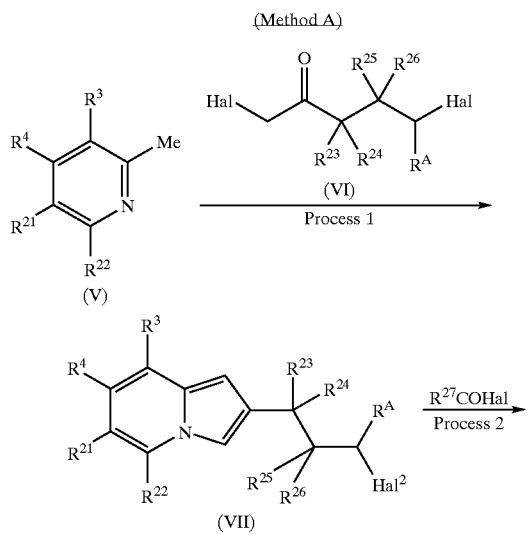

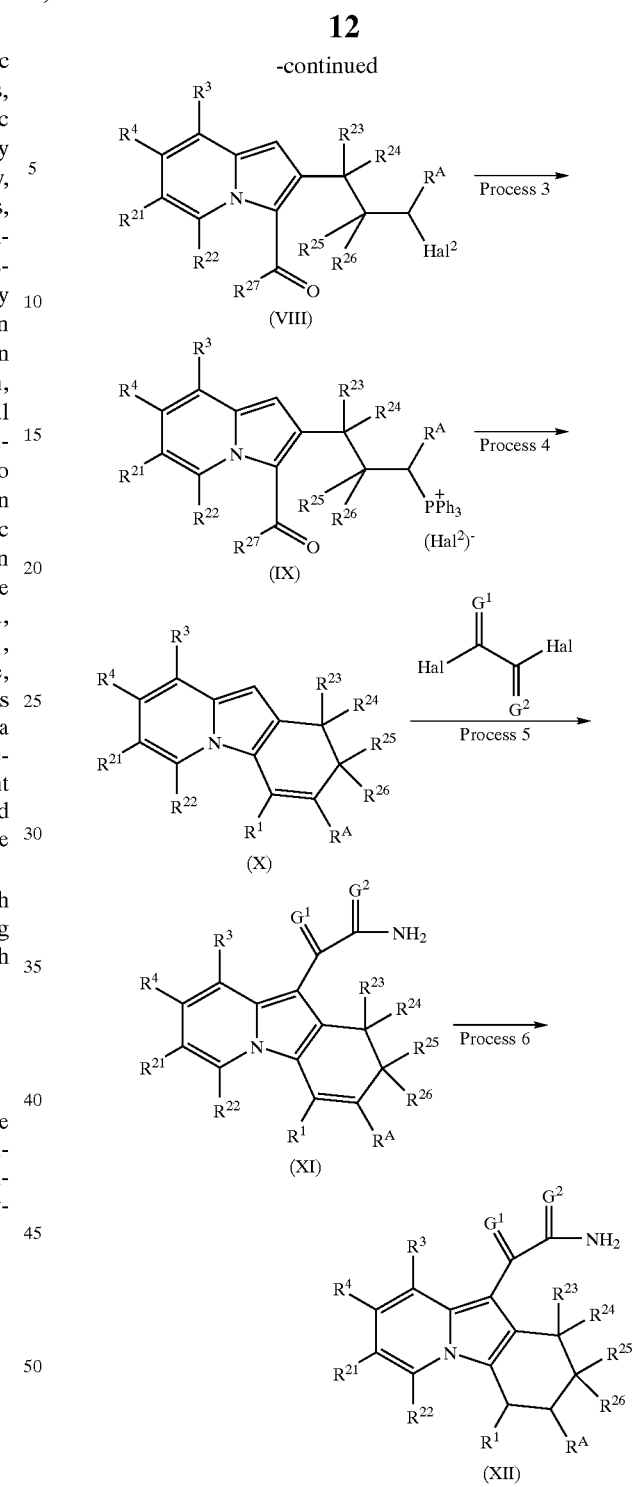

wherein $R^1$, $R^3$, $R^4$, $R^{21}$, $R^{22}$, $R^{23}$, $R^{24}$, $R^{25}$, $R^{26}$, $R^A$, $G^1$, and $G^2$ are as defined above;

$R^{27}$ is the precursor of $R^1$; Hal and $Hal^2$ are halogens.

(Process 1)

A mixture of the compound (V) and the compound (VI) is stirred at 40° C. to 90° C., preferably 50 to 70° C. for 3 to 36 h, preferably 12 to 24 h to give the quaternary salt. To a solution of the obtained quaternary salt in a solvent such as 1,2-dichloroethane or acetonitrile is added a base such as 1,8-diazabicyclo[5.4.0]-7-undecene (DBU) or triethylamine, and the resulting mixture is stirred at 40° C. to 90° C., preferably 50 to 70° C. for 3 to 36 h, preferably 12 to 24 h. After the reaction mixture is subjected to a usual work-up, the compound (VII) can be obtained.

The compound (V) is commercial available or can be synthesized in accordance with the method described in J. Med. Chem., 39, 3636–58(1996). The compound (VI) is commercial available.

(Process 2)

The present process is performed by Friedel-Crafts reaction. To a solution of the compound (VII) in a solvent such as 1,2-dichloroethane or dichloromethane are slowly added $R^{27}COHal$ and a Lewis acid such as $AlCl_3$, $SbF_5$, or $BF_3$ at −78° C. to 10° C., preferably −20° C. to ice bath, and the reaction mixture is stirred at −10° C. to 10° C., preferably 0° C. to 10° C. for 5 to 30 min, preferably 10 to 20 min. This reaction is performed without solvent by the dissolving the compound (VII) in $R^{27}COHal$ and in accordance the above-mentioned procedure. After the reaction mixture is subjected to a usual work-up, the compound (VIII) can be obtained (Ref: J. Med. Chem., 39, 3636–58(1996)).

(Process 3)

The present process includes the conversion of the compound (VIII) to the phosphonium salt (IX). A mixture of the compound (VIII) and triphenylphosphine in a solvent such as acetonitrile or toluene is reacted at 80 to 150° C., preferably 100 to 120° C. for 5 to 72 h, preferably 10 to 24 h to obtain the compound (IX).

(Process 4)

The present process is for constructing the ring by Wittig reaction. To a solution of the compound (IX) in a solvent such as acetonitrile or tetrahydrofuran is added a base such as 1,8-diazabicyclo[5.4.0]-7-undecene (DBU) or potassium t-butoxide and the reaction mixture is reacted at, 20 to 120° C., preferably 80 to 100° C. for 3 to 24 h, preferably 5 to 10 h to give the compound (X).

(Process 5)

To a solution of the compound (X) in a solvent such as 1,2-dichloromethane or tetrahydrofuran are added Hal—C(=$G^1$)—C(=$G^2$)—Hal(e.g., oxalyl chloride) and a base such as N-methylmorpholine or triethylamine, and the reaction mixture is stirred at 30 to 70° C., preferably 40 to 60° C. for 1 to 10 h, preferably, 3 to 6 h. The reaction mixture is poured into a cold aqueous ammonium solution and the resulting mixture is stirred for 5 to 30 min, preferably, 10 to 20 min. After the reaction mixture is subjected to a usual work-up, the compound (XI) can be obtained.

(Process 6)

The present process includes reduction of the double bond by hydrogenation. To a solution of the compound (XI) in a solvent such as tetrahydrofuran, methanol or ethyl acetate is added Palladium-Carbon catalyst, and the mixture is reacted under hydrogen atmosphere at room temperature for 1 to 5 h, preferably 1 to 2 h to yield the compound (XII).

(Method B)

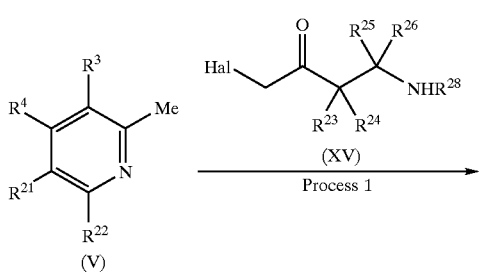

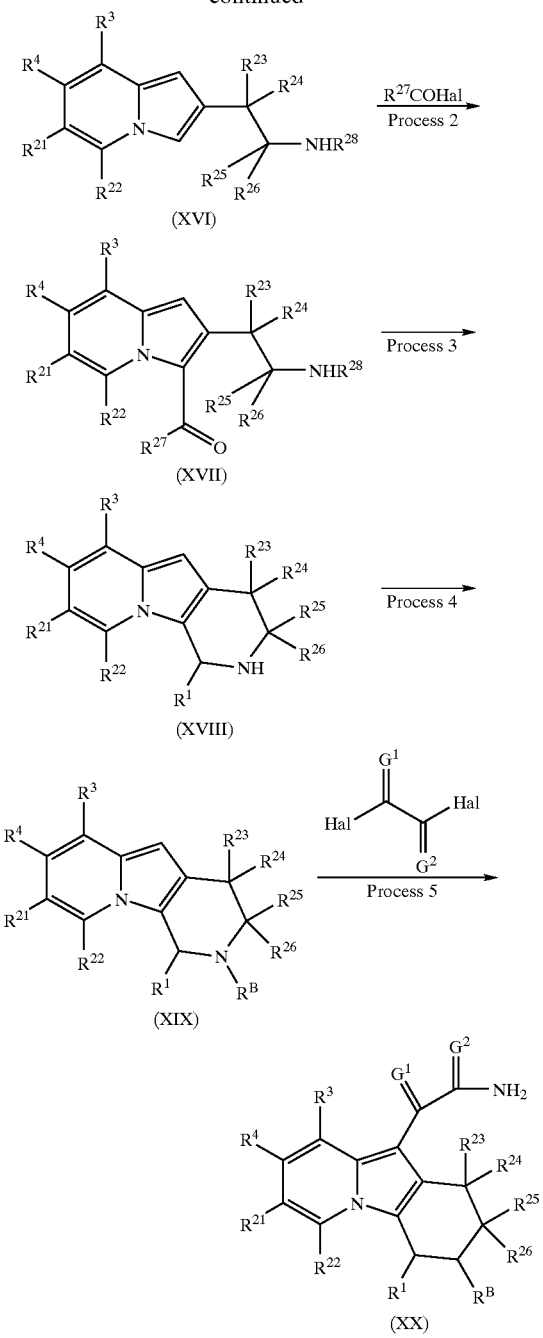

wherein $R^1$, $R^3$, $R^4$, $R^{21}$, $R^{22}$, $R^{23}$, $R^{24}$, $R^{25}$ $R^{26}$, $R^{27}$, $R^B$, $G^1$, $G^2$ and Hal are as defined above; $R^{28}$ is a protecting group such as benzyloxycarbonyl, or p-methoxybenzyloxycarbonyl)

(Process 1)

The present process may be carried out in accordance with the same procedure as that of the Method A—Process 1.

(Process 2)

The present process may be carried out in accordance with the same procedure as that of the Method A—Process 2.

(Process 3)

The present process is for constructing a piperidine ring by reductive amination. A solution of the compound (XVII)

in a solvent such as tetrahydrofuran or methanol is reacted in the presence of Palladium-Carbon catalyst under hydrogen atmosphere at room temperature for 1 to 10 h, preferably 2 to 5 h to give the compound (XVIII).

(Process 4)

The present step is for N-alkylation or N-acylation. A solution of the compound (XVIII) in tetrahydrofuran or dichloromethane in the presence of $R^B$—Hal and a base such as triethylamine or pyridine is reacted at 20 to 100° C., preferably 50 to 80° C. for 1 to 24 h, preferably 2 to 5 h to yield the compound (XIX).

(Process 5)

The present process may be carried out in accordance with the same procedure as that of the Method A—Process 5.

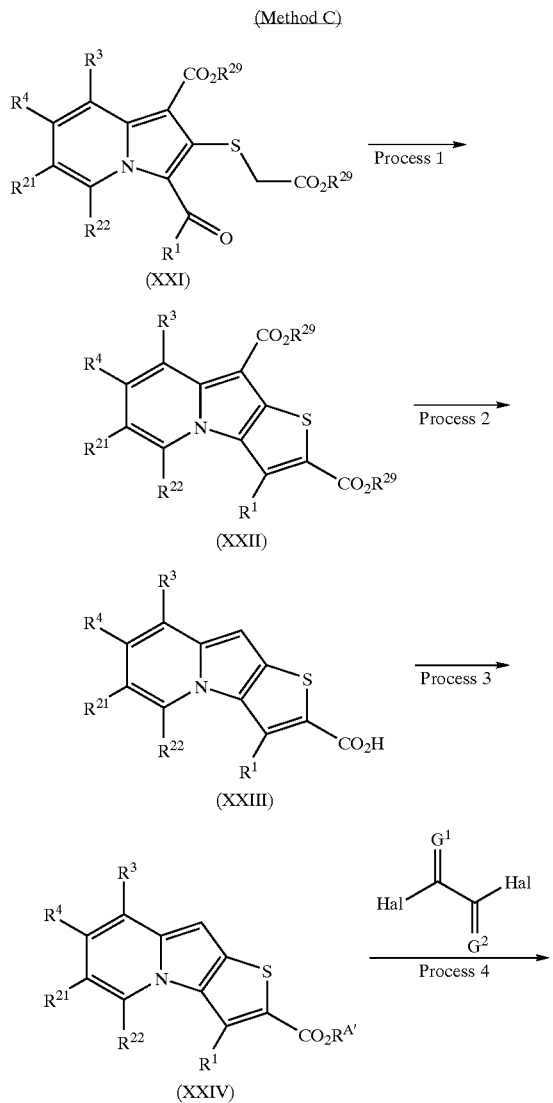

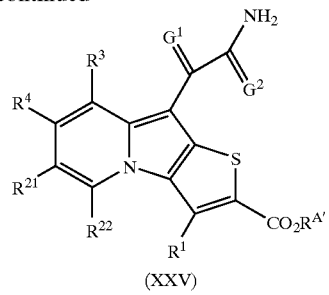

wherein $R^1$, $R^3$, $R^4$, $R^{21}$, $R^{22}$, $G^1$, $G^2$, and Hal are as defined above; $R^{29}$ and $R^{A'}$ are alkyl.

(Process 1)

The present step is for constructing a thiophen ring. A solution of the compound (XXI) in a solvent such as ethanol is reacted in the presence of a base such as DBU at 20 to 120° C., preferably 50 to 80° C. for 1 to 5 h, preferably 1 to 2 h to give the compound (XXII).

The compound (XXI) can be synthesized in accordance with the method described in Bull. Chem. Soc. Jpn., 62, 119 (1989)

(Process 2)

The present process is for hydrolysis of ester to carboxylic acid derivatives followed by decarboxylation.

Hydrolysis of the compound (XXII) in a solvent such as tetrahydrofuran, ethanol, dimethylformamide is carried out in the presence of a base such as sodium hydroxide, potassium hydroxide at 20 to 150° C., preferably 50 to 150° C. for 1 to 5 h, preferably 1 to 2 h.

Decarboxylation is carried out by the reaction of the above-mentioned carboxylic acid derivatives in solvent such as dimethyl sulfoxide or dimethylformamide at 50 to 200° C., preferably 100 to 150° C. for 1 to 5 h, preferably 1 to 2 h.

(Process 3)

The present process is for esterification of the carboxyl group of the compound (XXIII). It is carried out by the usual esterification (Ref:Protective groups in organic synthesis (second edition) p227–270).

(Process 4)

The present process may be carried out in accordance with the same procedure as that of the Method A—Process 5.

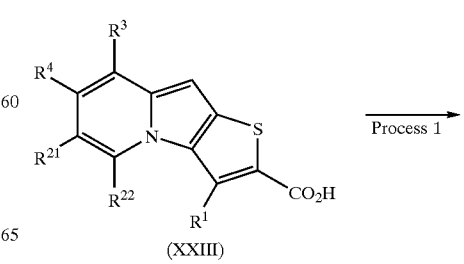

-continued

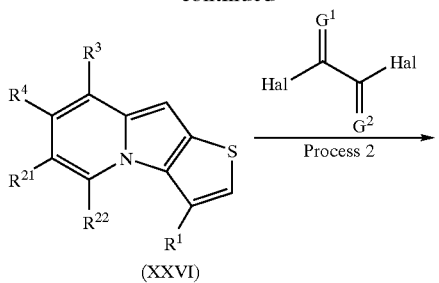

(XXVI)

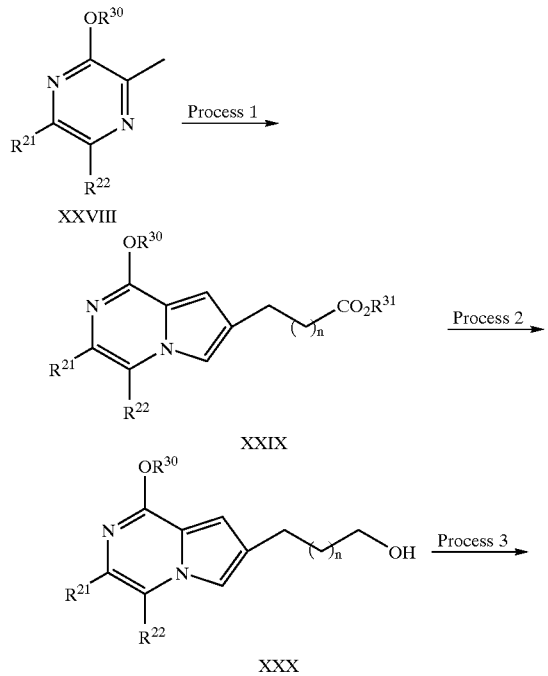

wherein $R^1$, $R^3$, $R^4$, $R^{21}$, $R^{22}$, $G^1$, $G^2$, and Hal are as defined above.

(Process 1)

The present process is for decarboxylation of the carboxylic group of the compound (XXIII). A solution of the compound (XXIII) in a solvent such as quinoline is reacted in the presence of a copper catalyst at 100 to 200° C., preferably 120 to 160° C. for 15 min to 2 h, preferably 30 min to 1 h to give the compound (XXVI).

(Process 2)

The present process may be carried out in accordance with the same procedure as that of the Method A—Process 5.

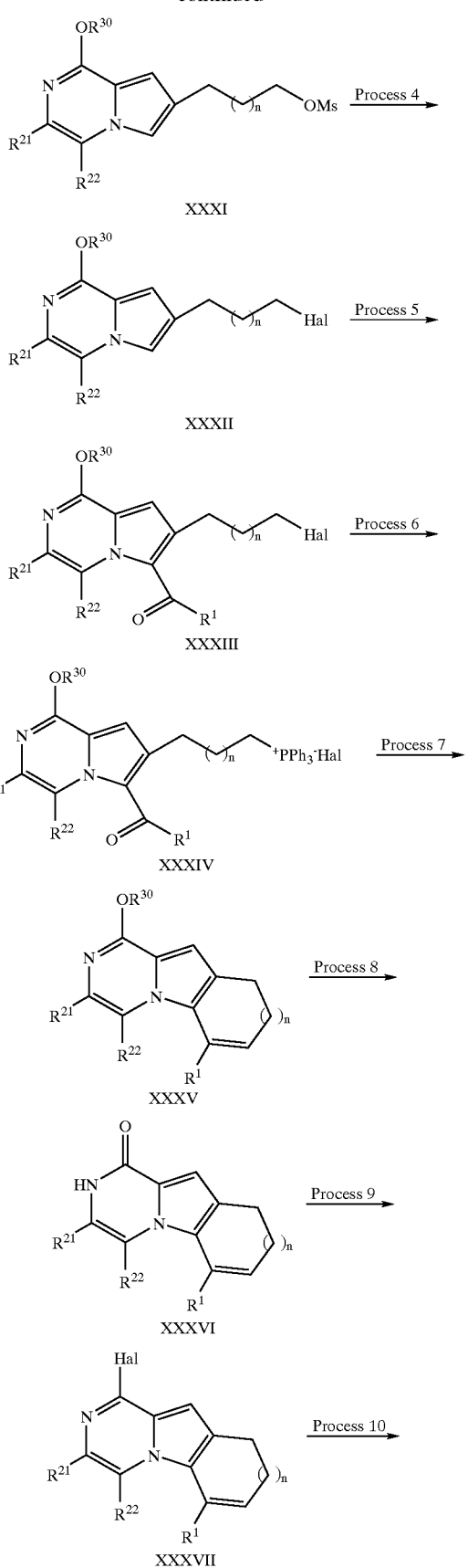

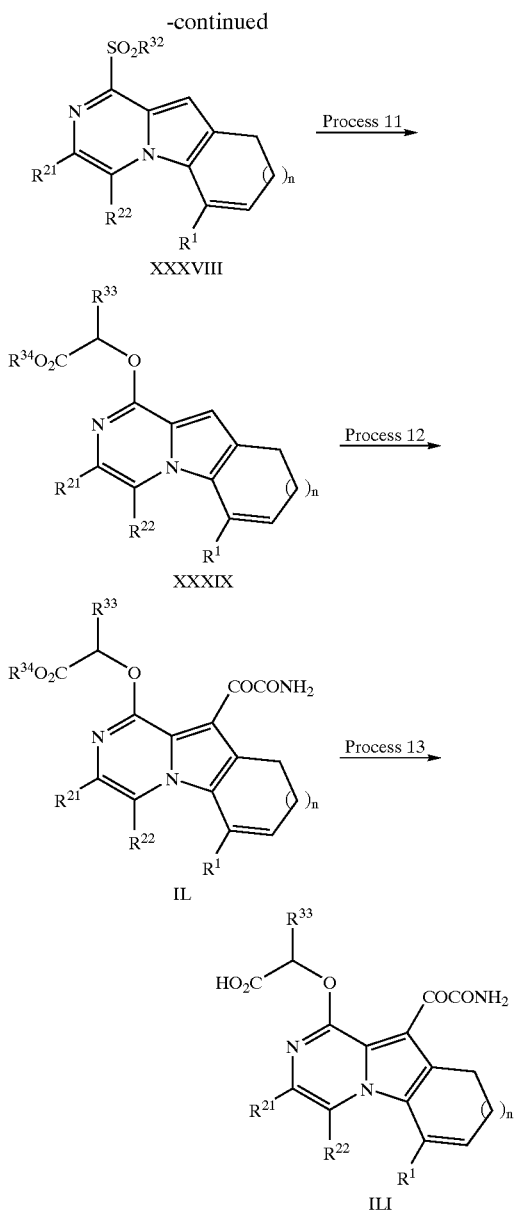

wherein $R^1$, $R^{21}$, $R^{22}$, and Hal are as defined above; $R^{30}$ is C1–C3 alkyl; $R^{31}$ is C1–C3 alkyl; $R^{32}$ is C1–C3 alkyl or optionally substituted aryl (e.g., tolyl); $R^{33}$ is C1–C3 alkyl; $R^{34}$ is a hydrogen atom or C1–C3 alkyl; n is a integer from 1 to 3; Ms is mesyl.

(Process 1)

The present step is for constructing a pyrrolo[1,2-a]pyrazine ring. A mixture of the compound (XXVIII) and Hal—$CH_2$—C(=O)—$CH_2$—$(CH_2)_n$—$CO_2R^{31}$ is stirred at 40° C. to 90° C., preferably 50° C. to 70° C. for 3 to 36 h, preferably 12 to 24 h to give the quaternary salt. To a solution of the obtained quaternary salt in a solvent such as 1,2-dichloroethane or acetonitrile is added a base such as 1,8-diazabicyclo[5.4.0]-7-undecene (DBU) or triethylamine, and the mixture is stirred at 40° C. to 90° C., preferably 60° C. to 80° C. for 1 to 10 h, preferably 1 to 5 h. After the reaction mixture is subjected to a usual work-up, the compound (XXIX) can be obtained.

(Process 2)

The present process is for reducing the ester group to alcohol. A solution of the compound (XXIX) in a solvent such as ether or tetrahydrofuran is reacted with a reducing agent such as lithium hydride, lithium aluminum hydride or lithium borohydride at 0° C. to 80° C., preferably 10° C. to 40° C. for 30 min to 10 h, preferably 1 h to 5 h to obtain the compound (XXX).

(Process 3)

The present process is for transforming the hydroxy group into —$OSO_2Me$. A solution of the compound (XXX) in a solvent such as dichloromethane or tetrahydrofuran is reacted with methanesulfonyl chloride in the presence of a base such as triethylamine or pyridine at −50° C. to 50° C., preferably −40° C. to 30° C. for 10 min to 5 h, preferably 30 min to 2 h to give the compound (XXXI).

(Process 4)

The present process is for transforming —$OSO_2Me$ into halogen. A solution of the compound (XXXI) in acetonitrile, acetone or dimethylformamide is reacted with a reagent such as lithium bromide or lithium chloride at 0° C. to 100° C., preferably 30° C. to 60° C. for 1 to 10 h, preferably 1 to 5 h to obtain the compound (XXXII).

(Process 5)

The present process is for introducing a substituent at 6-position of the pyrrolo[1,2-a]pyrazine by Friedel-Crafts reaction. To a solution of the compound (XXXII) in a solvent such as dichloromethane or chlorobenzene are added slowly $R^1$COHal and Lewis acid (e.g., $AlCl_3$, $SbF_5$, $BF_3$ and the like) at −78° C. to 10° C., preferably −20° C. to 0° C., and the mixture is stirred at −10° C. to 10° C., preferably, 0° C. to 10° C. for 30 min to 5 h, preferably 1 h to 3 h. After the reaction mixture is subjected to a usual work-up, the compound (XXIX) can be obtained.

(Process 6)

The present process is for preparing phosphonium salt. A mixture of the compound (XXXIII) and triphenylphosphine and the like in a solvent such as acetonitrile or toluene is reacted at 60° C. to 150° C., preferably 80° C. to 120° C. for 5 to 100 h preferably 10 to 70 h to give the compound (XXXIV).

(Process 7)

The present process is for constructing a ring by Wittig reaction. To a solution of the compound (XXXIV) in a solvent such as dichloromethane, acetonitrile, or tetrahydrofuran is added a base such as 1,8-dizabicyclo[5.4.0]-7-undecene (DBU), potassium t-butoxide, and the mixture is reacted at 20° C. to 120° C., preferably 30° C. to 100° C. for 1 to 24 h, preferably 3 to 10 h to obtain the compound (XXXV).

(Process 8)

The present process is for transforming the alkyloxy group at 1-position into ketone. An acid such as concentrated hydrochloric acid and the like is added to the compound (XXXV), and the mixture is stirred at 80° C. to 150° C., preferably 100° C. to 120° C. for 1 to 5 h, preferably 1 to 3 h. After the resulting product is subjected to a usual work-up, the compound (XXXVI) can be obtained.

(Process 9)

The present process is for transforming the ketone at 1-position into a halogen. A halogenating agent such as phosphorus oxychloride, phenylphosphonic dichloride and the like is added to the compound (XXXVI), and the mixture is stirred at 60° C. to 150° C., preferably 80° C. to 110° C. for 10 min to 3 h, preferably 30 min to 1 h. After the resulting product is subjected to an ordinary work-up, the compound (XXXVII) can be obtained.

(Process 10)

The present process is for transforming the halogen at 1-position into a sulfonyl group. To a solution of the compound (XXXVII) in ethanol is added $R^{32}SO_2Na$, and the mixture is refluxed for 10 to 50 h, preferably 24 to 36 h to give the (XXXVIII).
(Process 11)

The present process is for transforming the sulfonyl group at 1-position into alkyloxy group. A suspension of HOCH$(R^{33})CO_2R^{34}$, sodium hydride and potassium t-butoxide in a solvent such as tetrahydrofuran and the like is stirred at −20° C. to 50° C., preferably 0° C. to 30° C. for 15 min to 2 h, preferably 30 min to 1 h. To the solution is added the compound (XXXVIII), and the resulting mixture is stirred at −20° C. to 50° C., preferably 0° C. to 30° C. for 15 min to 5 h, preferably 30 min to 2 h to yield the compound (XXXIX).
(Process 12)

The present process is for introducing a substituent at 5-position. To a solution of the compound (XXXIX) in a solvent such as dichloromethane or tetrahydrofuran are added Hal—C(=O)—C(=O)—Hal (Hal is a halogen)(e.g., oxalyl chloride) and a base such as N-methylmorpholine or triethylamine and the reaction mixture is stirred at −30° C. to 70° C., preferably −20° C. to 40° C. for 10 min to 10 h, preferably, 10 min to 2 h. The reaction mixture is poured into an aqueous ammonium solution and the resulting mixture is subjected to a usual work-up to give the compound (IL) can be obtained.
(Process 13)

The present process is for hydrolysis. To a solution of the compound (IL) in a solvent such as methanol or tetrahydrofuran is added a base such as sodium hydroxide and the like, and the resulting mixture is stirred at 0° C. to 40° C., preferably 10° C. to 30° C. for 0.5 to 6 h, preferably 0.5 to 2 h to give the compound (ILI).

Where a compound of the present invention has an acidic or basic functional group, a variety of salts having higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)) Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, gluseptates, gluconates, glutamates, glycolialsanyrates, hexylresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like.

In the case where a compound of the present invention has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified streoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoisomers, and thereafter separating the mixture in accordance with a well-known manner.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). For instance, prodrugs each containing an acid derivative such as an ester which is prepared by reacting a basal acid compound with a suitable alcohol, or an amide which is prepared by reacting a basal acid compound with a suitable amine are well known by those skilled in the art. Simple aliphatic or aromatic esters derived from acid groups contained in the compounds according to the present invention are preferable prodrugs. More preferable is C1–C6 alkyl ester of carboxylic derivatives (e.g., methyl ester, ethyl ester). Double ester such as (acyloxy)alkyl ester or ((alkyloxycarbonyl)oxy)alkyl ester type prodrugs may be optionally manufactured.

The term "inhibit" means that release of fatty acid started by $sPLA_2$ decreases significantly by the compounds of the present invention from viewpoint of prevention and treatment of disease. The term "pharmaceutically acceptable" means that carriers, diluents, or additives are compatible with other ingredients in a formulation and are not harmful for recipients.

The compounds of the present invention exhibit $sPLA_2$ inhibiting activity as per the description of the experimental examples which will be described hereinafter. Accordingly, when a curatively effective amount of the compounds represented by the formulae (I), (II), and (III), the prodrug derivatives thereof, or their pharmaceutically acceptable salts, or their solvates is administered to any of mammals (including human being), it functions effectively as a curative medicine for diseases of septic shock, adult respiratory distress syndrome, pancreatitis, injury, bronchial asthma, allergic rhinitis, chronic rheumatism, arterial sclerosis, cerebral hemorrhage, cerebral infarction, inflammatory colitis, psoriasis, cardiac failure, cardiac infarction.

The compounds of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound according to the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

The dosage varies with the conditions of the disease, administration route, age and body weight of patient. In the case of oral administration, the dosage can generally be between 0.01 to 50 mg/kg/day for adult.

The following examples are provided to further illustrate the present invention and are not to be constructed as limiting the scope thereof.

Abbreviations described below are used in the following examples.

Me:methyl
Et:ethyl
Ph:phenyl
Bn:benzyl
DBU:1,8-diazabicyclo[5.4.0]-7-undecene

EXAMPLE

Example 1

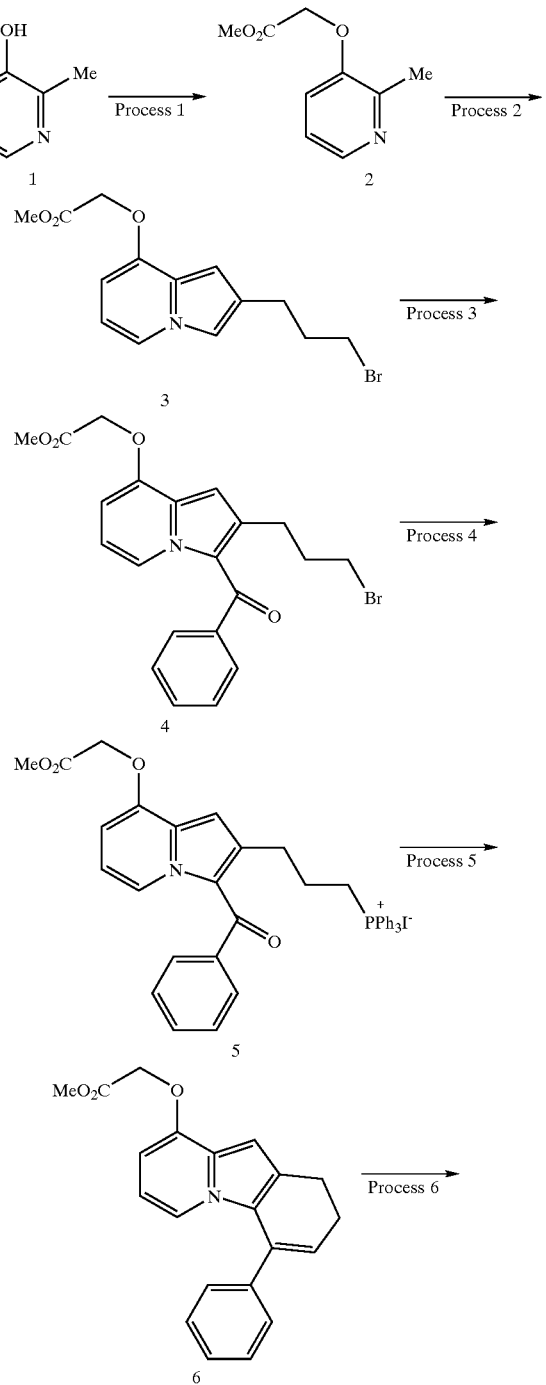

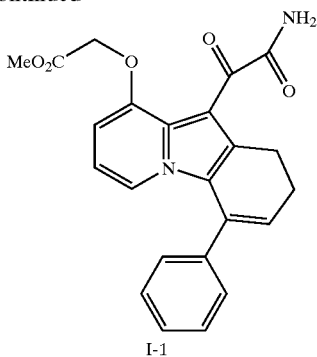

I-1

(Process 1)

To a solution of the compound (1) 10.9 g in tetrahydrofuran 200 ml was gradually added 60% sodium hydride 5.20 g in an ice bath. To the reaction mixture was added methyl bromoacetate 11.4 ml in an ice bath and the mixture was stirred at room temperature for 3.5 h. After the excess sodium hydride was decomposed with methanol, the resulting mixture was evaporated under reduced pressure to remove tetrahydrofuran. Water was added, the mixture was extracted with toluene, and the organic layer was dried over magnesium sulfate. The obtained residue was subjected to a silica gel (120 g) column chromatography. The fraction eluting with 20% ethyl acetate-toluene gave 13.46 g of crude product and then the distillation under reduced pressure gave the compound (2) 12.43 g as colorless oil (yield 68.6%). boiling point: 109–110° C. (1.5 mmHg).

$^1$H-NMR (CDCl$_3$) δ 2.54 (3H, s), 3.81 (3H, s), 4.66 (2H, s), 6.97 (1H, d of d), 7.07 (1H, d of d), 8.14 (1H, d of d).

(Process 2)

A solution of the compound (2) 3.85 g and 1,5-dibromo-2-pentanoen 5.18 g in dichloromethane 5 ml was heated at 65° C. in an oil bath for 2.5 h evaporating dichloromethane. To the product were added dichloroethane 100 ml and 2,6-lutidine 2.47 ml and the mixture was refluxed on an oil bath for 45.5 h. Water was added and the mixture was extracted with chloroform. The extracts were dried over magnesium sulfate and evaporated and then the obtained residue was subjected to 80 g of the silica gel column chromatography (eluted with chloroform) to obtain the compound (3) 1.68 g as colorless oil (yield 24.4%).

$^1$H-NMR (CDCl$_3$) δ 2.12 (2H, m), 2.83 (2H, t), 3.57 (2H, t), 3.82 (3H, s), 4.73 (2H, s), 5.85 (1H, d), 6.30 (1H, t), 6.48 (1H, brs), 7.14 (1H, brs), 7.54 (1H, d).

(Process 3)

A solution of the compound (3) 1.68 g, N,N-diisopropylethylamine 1.35 ml and benzoylchloride 0.90 ml in toluene 50 ml was refluxed in an oil bath for 2 h. To the reaction mixture were added water and 2N hydrochloric acid 2 ml and then the mixture was extracted with toluene. The extracts were dried over magnesium sulfate and evaporated and then the obtained residue was subjected to 40 g of the silica gel column chromatography (eluted with 20% ethyl acetate-toluene) to obtain the compound (4) 2.04 g as yellow oil (yield 91.8%).

$^1$H-NMR (CDCl3) δ 1.88 (2H, m), 2.43 (2H, t), 3.26 (2H, t), 3.84 (3H, s), 4.79 (2H, s), 6.33 (1H, d), 6.64 (1H, s), 6.70 (1H, d), 7.19–7.66 (5H, m), 9.19 (1H, d).

(Process 4)

A solution of the compound (4) 1.98 g, triphenylphosphine 1.46 g and potassium iodide 0.767 g in acetonitrile 40 ml was refluxed in an oil bath for 72 h. After acetonitrile was evaporated under reduced pressure, the residue was subjected to 51 g of the silica gel column chromatography (eluted with 5% methanol-chloroform) to obtain the compound (5) 3.41 g as yellow powder (yield 100%).

$^1$H-NMR (CDCl3) δ 1.65 (2H, m), 2.81 (2H, t), 3.39 (2H, m), 3.83 (3H, s), 4.79 (2H, s), 6.32 (1H, d), 6.66 (1H, d), 6.72 (1H, s), 7.32–7.80 (20H, m), 9.03 (1H, d).

(Process 5)

A solution of the compound (5) 2.93 g and DBU 1.21 g in acetonitrile 50 ml was refluxed in an oil bath for 24 h. After acetonitrile was evaporated under reduced pressure, water was added and the mixture was extracted with chloroform. The extracts were dried over magnesium sulfate and evaporated and then the obtained residue was subjected to 40 g of the silica gel column chromatography (eluted with chloroform) to obtain the compound (6) 0.613 g as yellow green oil (yield 46.4%).

$^1$H-NMR (CDCl3) δ 2.44 (2H, m), 2.87 (2H, t), 3.81 (3H, s), 4.73 (2H, s), 5.79 (1H, t), 5.81 (1H, d), 6.06 (1H, t), 6.64 (1H, s), 6.78 (1H, d), 7.26–7.39 (5H, m).

(Process 6)

To a solution of the compound (6) 603 mg in dichloromethane 20 ml was added oxalyl chloride 0.80 ml at −35° C. The mixture was refluxed at 65° C. for 40 min. The reaction mixture was added to cold concentrated aqueous ammonia 15 ml, then the mixture was extracted with chloroform. The extracts were dried over magnesium sulfate and evaporated and then the obtained residue was subjected to 30 g of the silica gel column chromatography (eluted with 10% acetonitrile-chloroform). The obtained compound was recrystallized from methanol-isopropanol to give the compound (I-1) 176 mg as a yellow crystal (yield 23.8%). m.p (decomp.p.): 225–227° C.

$^1$H-NMR (CDCl$_3$) δ 2.47 (2H, m), 3.04 (2H, t), 3.78 (3H, s), 4.72 (2H, s), 5.49 (1H, brs), 5.93 (1H, t), 6.21 (1H, d), 6.32 (1H, t), 6.64 (1H, brs), 6.92 (1H, d), 7.25–7.34 (5H, m).

Example 2

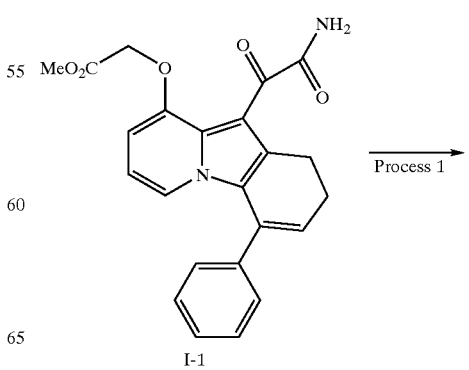

I-1

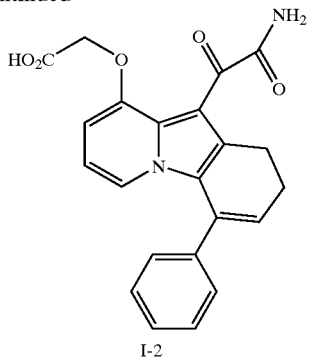

I-2

(Process 1)

To a solution of the compound (I-1) 50 mg in methanol 10 ml was added 1N aqueous sodium hydroxide solution 0.25 ml, and the reaction mixture was stirred at room temperature for 1.5 h. After evaporation of the solvent, 2N hydrochloric acid was added to acidify, and then the mixture was extracted with a mixed solution of ethyl acetate and tetrahydrofuran. The extracts were dried over magnesium sulfate and evaporated and then the obtained crude crystal 58 mg was recrystallized from tetrahydrofuran-isopropyl ether to give the compound (I-2) 44 mg as yellow crystal. (yield: 91.7%). m.p (decomp.p.): 228–230° C.

$^1$H-NMR (d6-DMSO) δ 2.42 (2H, m), 2.92 (2H, t), 4.73 (2H, s), 5.95 (1H, t), 6.42 (1H, d), 6.54 (1H, t), 6.83 (1H, d), 7.26–7.29 (2H, m), 7.39–7.45 (4H, m), 7.72 (1H, brs), 13.05 (1H, brs).

Example 3

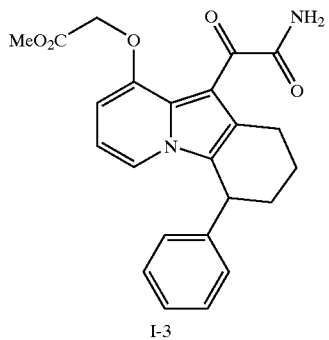

I-1

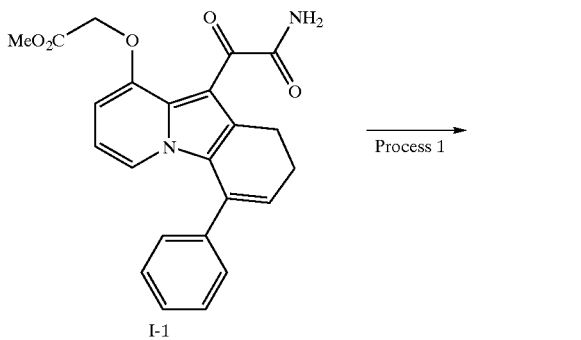

I-3

(Process 1)

A suspension of the compound (I-1) 116 mg and 10%Pd—C 30 mg in tetrahydrofuran 15 ml-methanol 15 ml was stirred at room temperature for 1.5 h under hydrogen atmosphere. After filtration of Pd—C and evaporation of filtrate under reduced pressure, the obtained crude crystal 129 mg was recrystallized from tetrahydrofuran-isopropyl ether to give the compound (I-3) 95 mg as yellow green crystal. (yield: 81.2%). m.p: 198–199° C.

$^1$H-NMR (CDCl3) δ 1.66–1.82 (2H, m), 1.95–2.02 (1H, m), 2.27 (1H, m), 2.81–3.14 (2H, m), 3.79 (3H, s), 4.18 (1H, t), 4.74 (2H, s), 5.58 (1H, brs), 6.28 (1H, d), 6.43 (1H, t), 6.58 (1H, brs), 7.04–7.09 (3H, m), 7.26 (3H, m).

Example 4

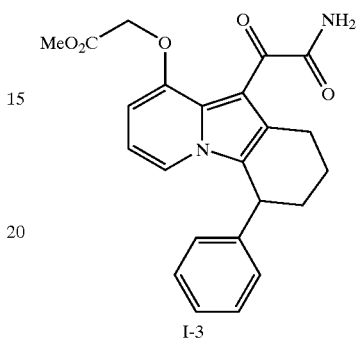

I-3

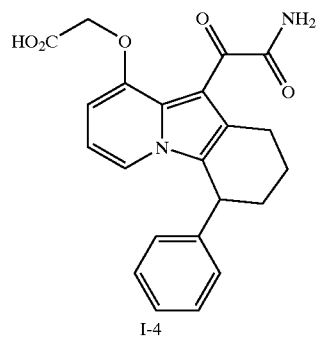

I-4

(Process 1)

Using the compound (I-3) as a starting material, compound (I-4) was synthesized in yield 85.1% in a manner similar to that described in Example 2. m.p.: 232–235° C.

$^1$H-NMR (d6-DMSO) δ 1.68 (2H, m), 1.90 (1H, m), 2.23 (1H, m), 2.73–2.83 (1H, m), 2.94–3.00 (1H, m), 4.42 (1H, m), 4.73 (2H, s), 6.46 (1H, d), 6.62 ( 1H, t), 7.01 (1H, d), 7.18–7.32 (6H, m), 7.65 (1H, brs), 13.00 (1H, brs).

Example 5

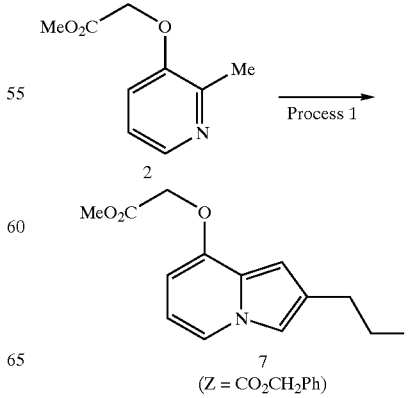

2

7
(Z = CO$_2$CH$_2$Ph)

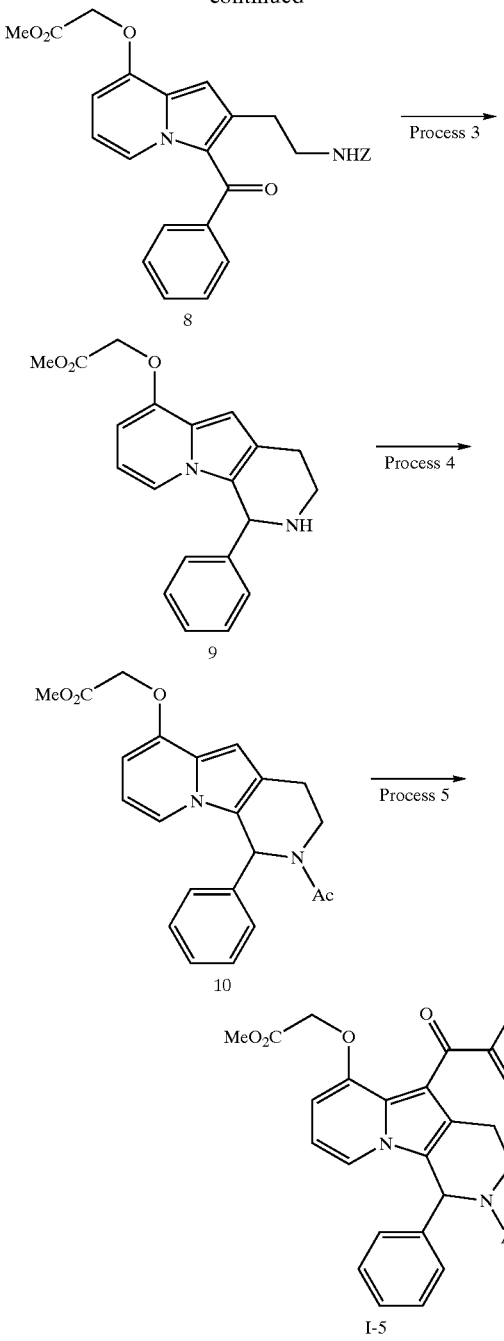

(Process 1)

A solution of the compound (2) 2,50 g, and 1-bromo-4-benzyloxycarbonylamino-2-butanone 4.14 g in dichloromethane 5 ml was heated at 65° C. in an oil bath for 2.5 h evaporating dichloromethane. To the product were added dichloroethane 50 ml and DBU 2.52 g and the mixture was refluxed on an oil bath for 1.5 h. Water was added and the mixture was extracted with chloroform. The extracts were dried over magnesium sulfate and evaporated and then the obtained residue was subjected to 30 g of the silica gel column chromatography (eluted with 5% acetonitrile-chloroform). The obtained crude crystal 5.74 g was recrystallized from ether-isopropyl ether to give the compound (7) 4.65 g as white crystal. (yield: 88.2%). m.p: 48–50° C.

$^1$H-NMR (CDCl3) δ 2.86 (2H, t), 3.50 (2H, q), 3.81 (3H, s), 4.73 (2H, s), 4.83 (1H, brs), 5.09 (2H, s), 5.86 (1H, d), 6.31 (1H, t), 6.49 (1H, brs), 7.11 (1H, brs), 7.34 (5H, s), 7.53 (1H, d).

(Process 2)

A solution of the compound (7) 2.00 g, 4-methylmorpholine 1.15 ml, benzoylchloride 0.91 ml in 1,2-dichloroethane 30 ml was refluxed in an oil bath for 1 h. To the reaction mixture were added water and aqueous ammonia 0.6 ml and then the mixture was extracted with chloroform. The extracts were dried over magnesium sulfate and evaporated and then the obtained residue was subjected to 20 g of the silica gel column chromatography (eluted with 5% acetonitrile-chloroform). The obtained crude crystal 2.86 g was recrystallized from acetone-isopropyl ether to give the compound (8) 2.15 g as white crystal. (yield: 84.5%). m.p: 103.5–104° C.

$^1$H-NMR (CDCl3) δ 2.51 (2H, t), 3.29 (2H, m), 3.83 (3H, s), 4.62 (1H, brs), 4.79 (2H, s), 5.04 (2H, s), 6.33 (1H, d), 6.66 (1H, brs), 6.67 (1H, t), 7.32 (5H, s), 7.29–7.62 (5H, m), 9.10 (1H, d).

(Process 3)

A suspension of the compound (8) 2.14 g and 10%Pd—C 0.43 g in tetrahydrofuran 22 ml-methanol 22 ml was stirred at room temperature for 4 h under hydrogen atmosphere. After filtration of Pd—C, the filtrate was evaporated of filtrate under reduced pressure. The obtained residue was dissolved in CHCl$_3$, then it was subjected to 22 g of the silica gel column chromatography (eluted with 5% methanol-chloroform). The obtained crude crystal 1.63 g was recrystallized from tetrahydrofuran-isopropyl ether to give the compound (9) 1.26 g as light yellow crystal. (yield: 84.6%). m.p.: 125–127° C.

$^1$H-NMR (CDCl3) δ 2.89 (2H, t), 2.96–3.22 (2H, m), 3.01 (3H, s), 4.74 (2H, s), 5.23 (1H, s), 5.84 (1H, d), 6.13 (1H, t), 6.60 (1H, s), 6.79 (1H, d), 7.13–7.32 (5H, m).

(Process 4)

To a solution of the compound (9) 300 mg and triethylamine 0.15 ml in chloroform 5 ml was added acetyl chloride 77 mg in an ice bath and the mixture was stirred for 15 min. To the reaction mixture was added water and then the mixture was extracted with chloroform. The extracts were dried over magnesium sulfate and evaporated and then the obtained residue was subjected to 5 g of the silica gel column chromatography (eluted with 10% acetonitrile-chloroform). The obtained crude crystal 405 mg was recrystallized from tetrahydrofuran-isopropyl ether to give the compound (10) 302 mg as white crystal. (yield: 89.6%). m.p: 146–147° C.

$^1$H-NMR (CDCl3) δ 2.20 (3H, s), 2.82–3.11 (2H, m), 3.32–3.86 (2H, m), 3.82 (3H, s), 4.76 (2H, s), 5.89 (1H, d), 6.24 (1H, t), 6.60 (1H, brs), 6.96 (1H, d), 7.10 (1H, s), 7.16–7.30 (5H, m).

(Process 5)

To a solution of oxalyl chloride 0.33 ml in dichloromethane 5 ml were added the compound (10) 284 mg and 4-methylmorpholine 0.165 ml in dichloromethane 5 ml at −15° C. and the mixture was stirred for 30 min. The reaction mixture was added to a solution mixed with cold concentrated aqueous ammonia 3 ml and chloroform 5 ml, the mixture was extracted with chloroform. The extracts were dried over magnesium sulfate and evaporated and then the obtained residue was subjected to 5 g of the silica gel column chromatography (eluted with 5% methanol-chloroform). The obtained crude crystal 398 mg was recrystallized from acetone-isopropyl ether to give the compound (I-5) 329 mg as a yellow crystal (yield 91.6%). m.p: 171–172° C.

¹H-NMR (CDCl3) δ 2.17 (3H, s), 2.20 (3H, s), 3.11–3.15 (1H, m), 3.80 (3H, s), 4.76 (2H, s), 5.83 (1H, brs), 6.36 (1H, d), 6.50 (1H, t), 5.59 (1H, brs), 7.09 (1H, s), 7.28–7.34 (5H, m), 6.58 (1H, brs).

Example 6

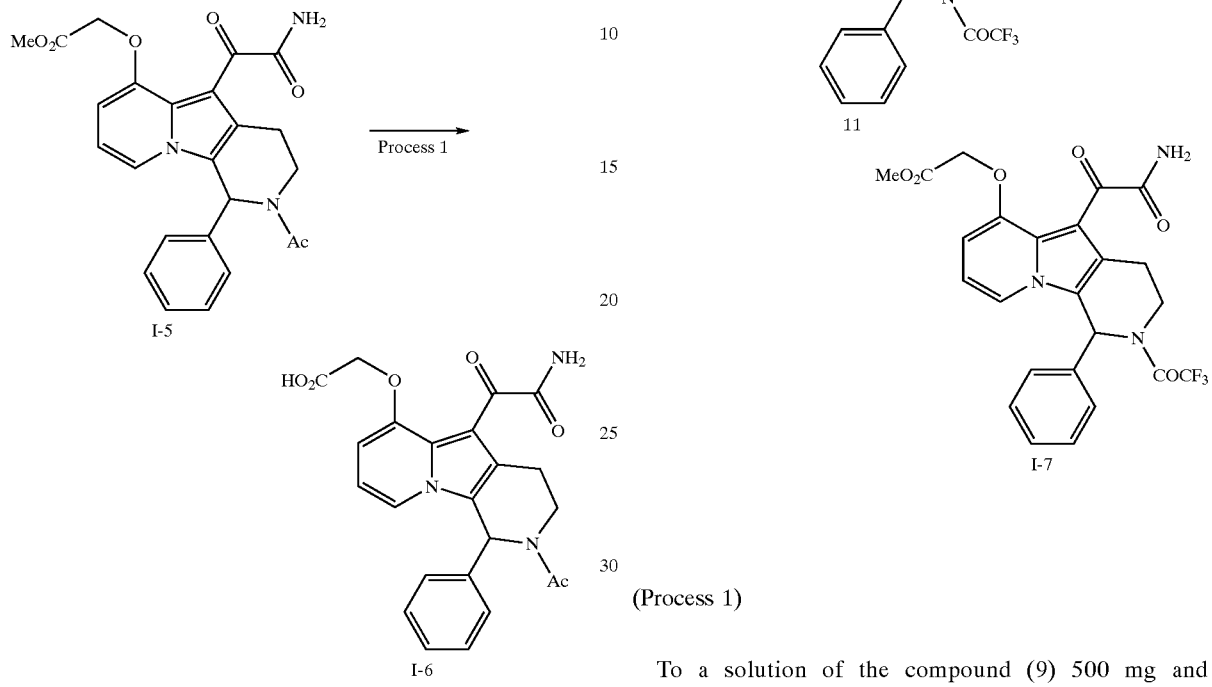

(Process 1)

Using the compound (I-5) as a starting material, compound (I-6) was synthesized in yield 84.1% in a manner similar to that described in Example 2. yellow crystal. m.p.: 236–238° C.

¹H-NMR (CDCl3) δ 2.15 (3H, s), 3.01–3.96 (4H, m), 4.76 (2H, s), 6.54 (1H, d), 6.70 (1H, t), 7.04 (1H, s), 7.11–7.36 (5H, m), 7.36 (1H, d), 7.71 (1H, s).

Example 7

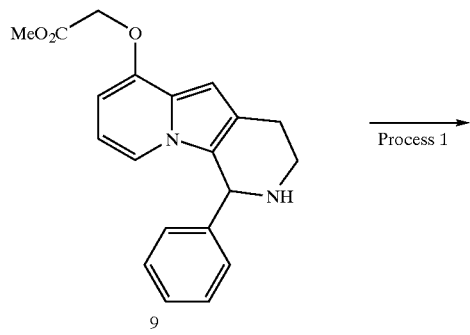

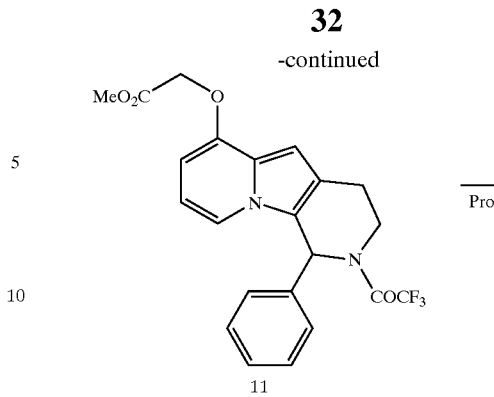

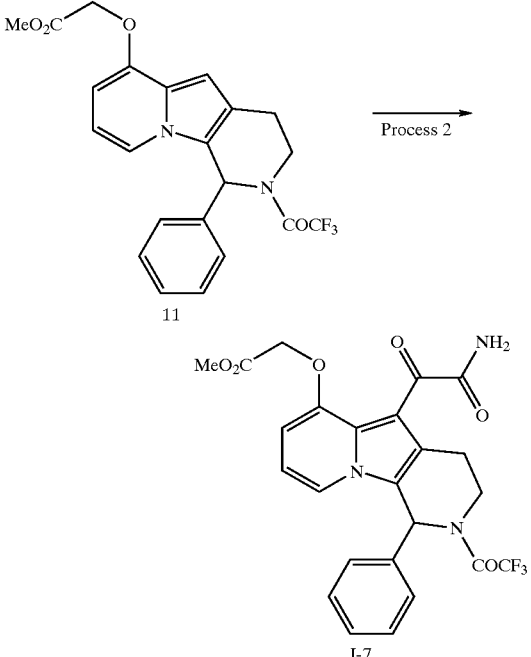

(Process 1)

To a solution of the compound (9) 500 mg and 4-methylmorpholine 0.4 ml in chloroform 10 ml was added trifluoroacetic anhydride 0.25 ml in an ice bath and the mixture was stirred for 15 min. To the reaction mixture was added water and then the mixture was extracted with chloroform. The extracts were dried over magnesium sulfate and evaporated and then the obtained residue was subjected to 18 g of the silica gel column chromatography (eluted with chloroform). The obtained crude crystal 659 mg was recrystallized from tetrahydrofuran-isopropyl ether to give the compound (11) 545 mg as white crystal. (yield: 84.8%). m.p: 129–130° C.

¹ H-NMR (CDCl3) δ 2.92–3.17 (2H, m), 3.43–3.51 (1H, m), 3.83 (3H, s), 4.00–4.06 (1H, m), 4.76 (2H, s), 5.92 (1H, d), 6.27 (1H, t), 6.61 (1H, brs), 6.94 (1H, d), 6.97 (1H, s), 7.17–7.34 (5H, m).

(Process 2)

Using the compound (11) as a starting material, compound (I-7) was synthesized in yield 95.7% in a manner similar to that described in Example 5—Process 5. yellow crystal. m.p.: 124–127° C.

¹H-NMR (CDCl3) δ 1.13 and 1.21 (3H, d), 3.18–3.21 (2H, m), 3.42–3.52 and 4.05–4.10 (2H, m), 3.65 (1H, m), 3.80 (3H, s), 4.77 (2H, s), 5.56 (1H, brs), 6.38 (1H, d), 6.58 (1H, brs), 6.59 (1H, t), 6.94 (1H, s), 7.11 (1H, d), 7.26–7.37 (5H, m).

Example 8
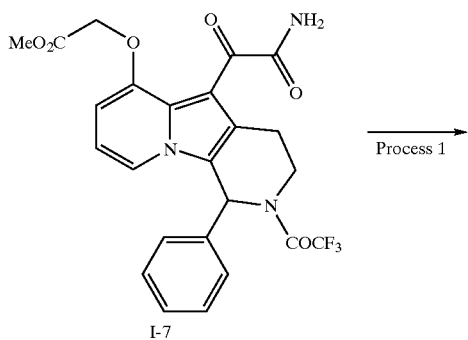
I-7
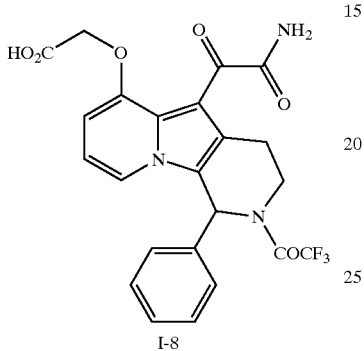
I-8
(Process 1)
Using the compound (I-7) as a starting material, compound (I-8) was synthesized in yield 38.0% in a manner similar to that described in Example 2. yellow crystal. decomp.p.: 215–216° C.
$^1$H-NMR (d6-DMSO) δ 2.90–3.58 (3H, m), 3.98–4.05 (1H, m), 4.78 (2H, s), 6.58 (1H, d), 6.73 (1H, t), 7.06 (1H, s), 7.17–7.42 (5H, m), 7.46 (1H, s), 7.74 (1H, s).
Example 9
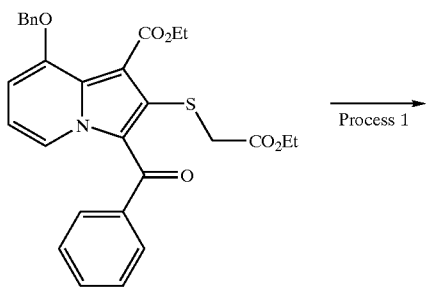
12
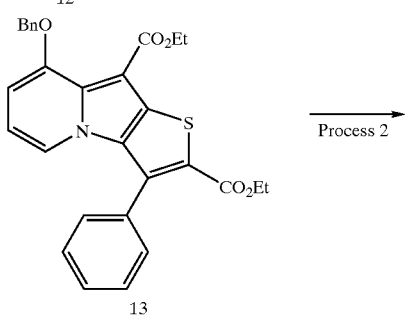
13
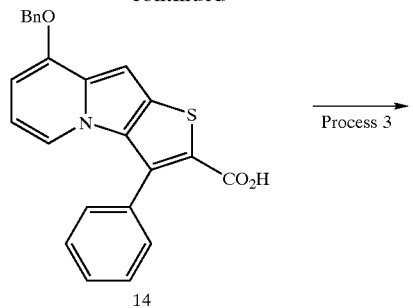
14
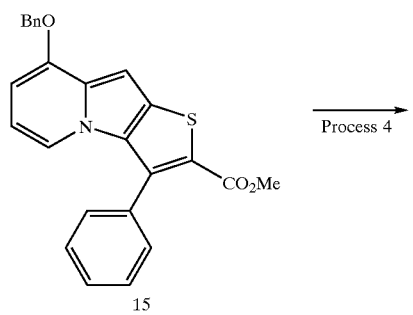
15
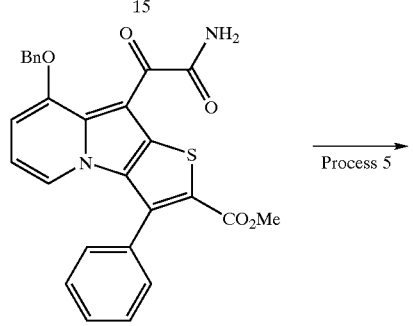
16
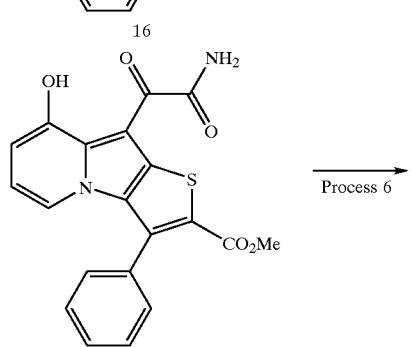
17
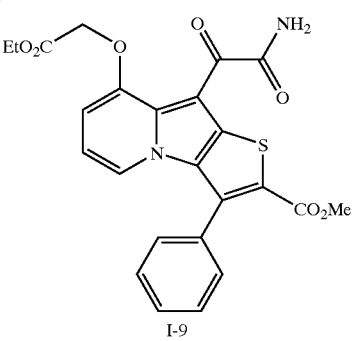
I-9
Using 3-benzyloxypyridine as a starting material, compound (12) was synthesized in accordance with the report of Kakei et. al. [Bul. Chem. Soc. Jpn., 62, 119 (1989)].

(12):

¹H-NMR (CDCl₃) 1.08 (3H, t, J=7.2 Hz), 1.14 (3H, t, J=7.2 Hz), 3.37 (2H, s), 3.99 (2H, q, J=7.2 Hz), 4.06 (2H, q, J=7.2 Hz), 5.18 (2H, s), 6.54 (1H, d, J=7.5 Hz), 6.75 (1H, t, J=7.5 Hz), 7.36–7.75 (10H), 8.84 (1H, d, J=7.5 Hz).

To a solution of the compound (12) 5.3 g (10.2 mmol) in ethanol 50 ml was added DBU 1.9 ml (12.7 mmol) and the mixture was refluxed for 15 min. Crystal was filtrated and washed with ethanol and diethyl ether successively. After drying, the compound(13)(3.22 g, yield: 61%) was obtained as yellow powder.

¹H-NMR (CDCl₃) 1.16 (3H, t, J=7.2 Hz), 1.39 (3H, t, J=7.2 Hz), 4.18 (2H, q, J=7.2 Hz), 4.38 (2H, q, J=7.2 Hz), 5.31 (2H, s), 6.37 (1H, t, J=7.5 Hz), 6.50 (1H, d, J=7.5 Hz), 7.25–7.56 (11H).

(Process 2)

To a solution of the compound (13) 3.22 g (6.2 mmol) in dimethylformamide 10 ml was added 50% aqueous sodium hydroxide solution 5 ml, and the mixture was stirred at 100° C. for 1.5 h. To the reaction mixture was added 2N hydrochloric acid to acidify, and then precipitated crystal was filtrated and dried. A solution of the obtained crystal in dimethylformamide 25 ml was stirred at 135° C. for 1.5 h. The reaction solution was diluted with water and the mixture was extracted with ethyl acetate. The extracts were washed with saturated brine, dried over magnesium sulfate and evaporated. Purification of silica gel chromatography gave the compound (14) (2.13 g, yield: 85%) as green yellow powder.

¹H-NMR (DMSO-d₆) δ 5.29 (2H, s), 6.39 (1H, t, J=7.5 Hz), 6.49 (1H, d, J=7.5 Hz), 6.89 (1H, s), 7.00 (1H, d, J=7.5 Hz), 7.35–7.54 (10H).

(Process 3)

Through a solution of the compound (14) 500 mg (1.25 mmol) in a solution mixed with dichloromethane 30 ml and ethanol 20 ml was blown diazomethane at 0° C. After the reaction was completed, evaporation of the solvent gave the compound (15) (494 mg, yield: 95%) as green powder.

¹H-NMR (DMSO-d₆) δ 3.62 (3H, s), 5.29 (2H, s), 6.43 (1H, t, J=7.2 Hz), 6.52 (1H, d, J=7.2 Hz), 6.91 (1H, s), 7.05 (1H, d, J=7.2 Hz), 7.35–7.56 (10H).

(Process 4)

To a solution of oxalyl chloride 238 mg (1.88 mmol) in tetrahydrofuran 10 ml was added dropwise the compound (15) 494 mg (1.19 mmol) in tetrahydrofuran 10 ml at 0° C. and the reaction mixture was stirred at 0° C. for 3 h. To the solution was added 28% aqueous ammonia solution 2 ml and the reaction mixture was stirred more 5 min. The reaction mixture was poured into water, then the mixture was extracted with ethyl acetate. The extracts were washed with saturated brine, dried over magnesium sulfate and evaporated. Purification of silica gel chromatography gave the compound (16) (570 mg, yield: 100%) as yellow powder.

¹H-NMR (CDCl₃) 3.74 (3H, s), 4.87 (1H, brs), 5.22 (2H, s), 6.20 (1H, brs), 6.52 (1H, t, J=6.9 Hz), 6.67 (1H, d, J=6.9 Hz), 7.31 (1H, d, J=6.9 Hz), 7.38–7.55 (10H).

(Process 5)

To a solution of the compound (16) 252 mg (0.52 mmol) in tetrahydrofuran 15 ml was added 10%Pd—C 50 mg. The reaction mixture was stirred under hydrogen gas for 1 h. After the reaction was completed, the catalyst was filtrated and washed with tetrahydrofuran. The solvent was evaporated and the residue was diluted with diethyl ether. Filtration of the precipitated crystal gave the compound (17) (186 mg, yield: 90%) as orange powder.

¹H-NMR (DMSO-d₆) 3.66 (3H, s), 7.00 (1H, t, J=6.2 Hz), 7.09 (1H, d, J=6.2 Hz), 7.21 (1H, d, J=6.2 Hz), 7.45–7.59 (5H), 8.08 (1H, brs), 8.39 (1H, brs).

(Process 6)

To a solution of the compound (17) 170 mg (0.43 mmol) in dimethylformamide 4 ml were added potassium carbonate 179 mg (1.3 mmol), ethyl bromoacetate 79 mg (0.47 mmol), and potassium iodide 15 mg (0.09 mmol). The reaction mixture was stirred at room temperature for 2 h, and then poured into water and to acidify with 1N hydrochloric acid. The resulting mixture was extracted with ethyl acetate, and the extracts were dried over magnesium sulfate and evaporated. Purification of silica gel chromatography gave the compound (I-9) (189 mg, yield: 91%) as yellow powder.

¹H-NMR (DMSO-d₆) δ 1.21 (3H, t, J=7.2 Hz), 3.66 (3H, s), 4.17 (2H, q, J=7.2 Hz), 4.95 (2H, s), 6.86 (1H, t, J=7.5 Hz), 6.94 (1H, d, J=7.5 Hz), 7.29 (1H, d, J=7.5 Hz), 7.47 (1H, brs), 7.50–7.59 (5H), 7.90 (1H, brs).

Example 10

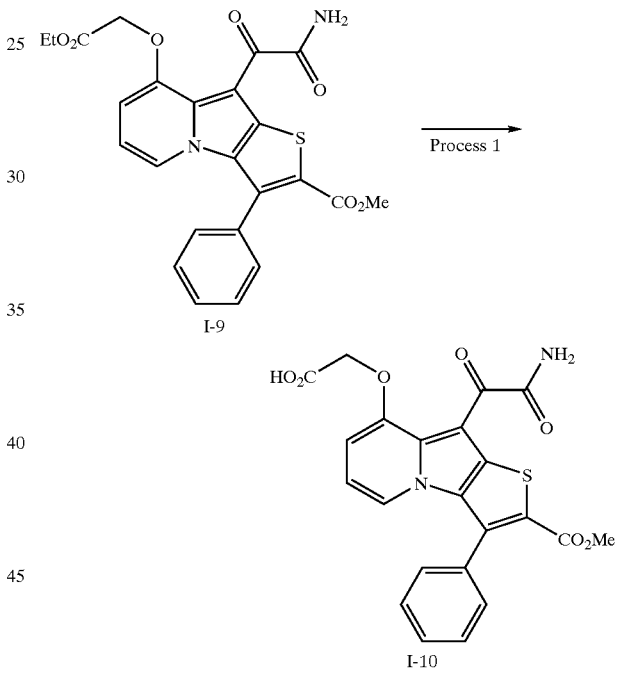

(Process 1)

To a solution of the compound (I-9) 140 mg (0.29 mmol) in methanol 5 ml was added 1N aqueous sodium hydroxide solution 0.44 ml, and the reaction mixture was stirred at room temperature for 1.5 h. To the reaction mixture was added 2N hydrochloric acid to acidify. The precipitated crystal was filtrated, washed with water and diethyl ether successively, and dried to give the compound (I-10) (115 mg, yield: 86%) as yellow powder.

¹H-NMR (DMSO-d₆) δ 3.66 (3H, s), 4.86 (2H, s), 6.85 (1H, t, J=6.6 Hz), 6.90 (1H, d, J=6.6 Hz), 7.28 (1H, d, J=6.6 Hz), 7.49–7.59 (6H), 7.90 (1H, brs).

Example 11

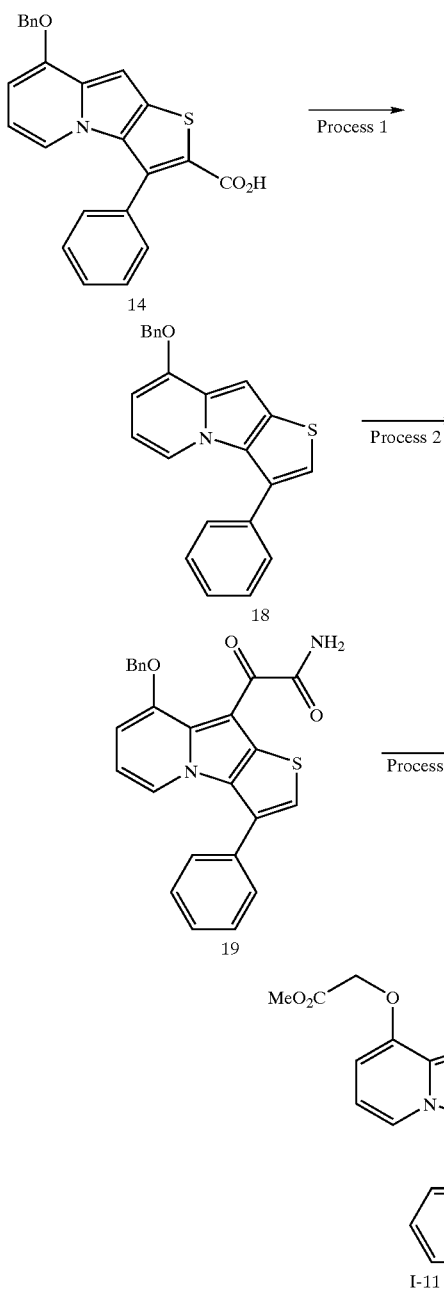

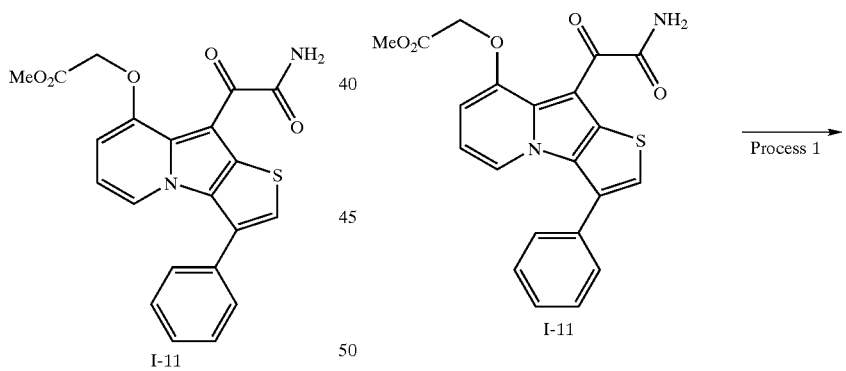

(Process 1)

To a solution of the compound (14) 800 mg (2.0 mmol) in quinoline 4 ml was added copper powder 80 mg, then the mixture was stirred at 165° C. for 45 min. The reaction mixture was diluted with chloroform, and washed with 2N hydrochloric acid. The extracts were dried over magnesium sulfate and evaporated. Purification of silica gel chromatography gave the compound (18) (543 mg, yield 77%) as yellow green powder.

$^1$H-NMR (CDCl$_3$) δ 5.22 (2H, s), 6.11 (1H, d, J=7.2 Hz), 6.22 (1H, t, J=7.2 Hz), 6.94 (2H, s), 7.34–7.58 (10H), 7.64 (1H, d, J=7.2 Hz).

(Process 2)

To a solution of oxalyl chloride 284 mg (2.24 mmol) in tetrahydrofuran 10 ml was added slowly a solution of the compound (18) 530 mg (1.49 mmol) in tetrahydrofuran 10 ml at 0° C. and the reaction mixture was stirred at 0° C. for 30 min. To the solution was added 28% aqueous ammonia 1 ml and the reaction mixture was stirred more 5 min. The mixture was diluted with water, the mixture was extracted with ethyl acetate. The extracts were washed with saturated brine, dried over magnesium sulfate and evaporated. Purification of silica gel chromatography gave the compound (19) (616 mg, yield 97%) as yellow powder.

$^1$H-NMR (DMSO-d$_6$) δ 5.40 (2H, s), 6.70 (1H, d, J=6.6 Hz), 6.77 (1H, t, J=6.6 Hz), 7.28–7.60 (10H), 7.42 (1H, brs), 7.44 (1H, s), 7.73 (1H, d, J=6.6 Hz), 7.96 (1H, brs).

(Process 3)

To a solution of the compound (19) 300 mg (0.70 mmol) in dichloromethane 20 ml was added, 1M boron tribromide-dichloromethane 3.5 ml in under ice cooling and the mixture was stirred at room temperature for 1 h. The reaction mixture was poured into water and the mixture was extracted with chloroform. The extracts were dried over magnesium sulfate and evaporated. To a solution of the obtained residue as red powder (160 mg) in dimethylformamide 4 ml were added potassium carbonate 197 mg (1.43 mmol), methyl bromoacetate 81 mg (0.53 mmol) and potassium iodide 16 mg (0.10 mmol). The reaction mixture was stirred at room temperature for 4 h, and then poured into 2N hydrochloric acid. The resulting mixture was extracted with ethyl acetate, and the extracts were dried over magnesium sulfate and evaporated. Purification of silica gel chromatography gave the compound (I-11) (176 mg, yield:61%) as white powder.

$^1$H-NMR (DMSO-d$_6$) δ 3.72 (3H, s), 4.96 (2H, s), 6.85 (2H, m), 7.39 (1H, brs), 7.46 (1H, s), 7.51–7.63 (5H), 7.82 (3H, m).

Example 12

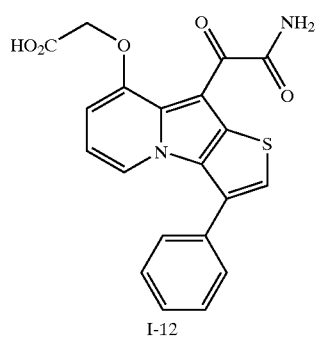

(Process 1)

To a solution of the compound (I-11) 140 mg (0.34 mmol) in a mixed solution of methanol 6 ml and tetrahydrofuran 2 ml was added 1N aqueous sodium hydroxide solution 0.51 ml, and the reaction mixture was stirred at room temperature for 40 min. To the reaction mixture was added 2N hydrochloric acid to acidify, and then precipitated crystal was filtrated and washed with water and diethyl ether successively, and dried. The compound (I-12) (115 mg yield 85%) was given as yellow powder.

$^1$H-NMR (DMSO-$d_6$) δ 4.85 (2H, s), 6.79 (1H, d, J=7.2 Hz), 6.87 (1H, t, J=7.2 Hz), 7.43 (1H, brs), 7.46 (1H, s), 7.51–7.62 (5H), 7.81 (1H, d, J=7.2 Hz), 7.83 (1H, brs).

Example 13

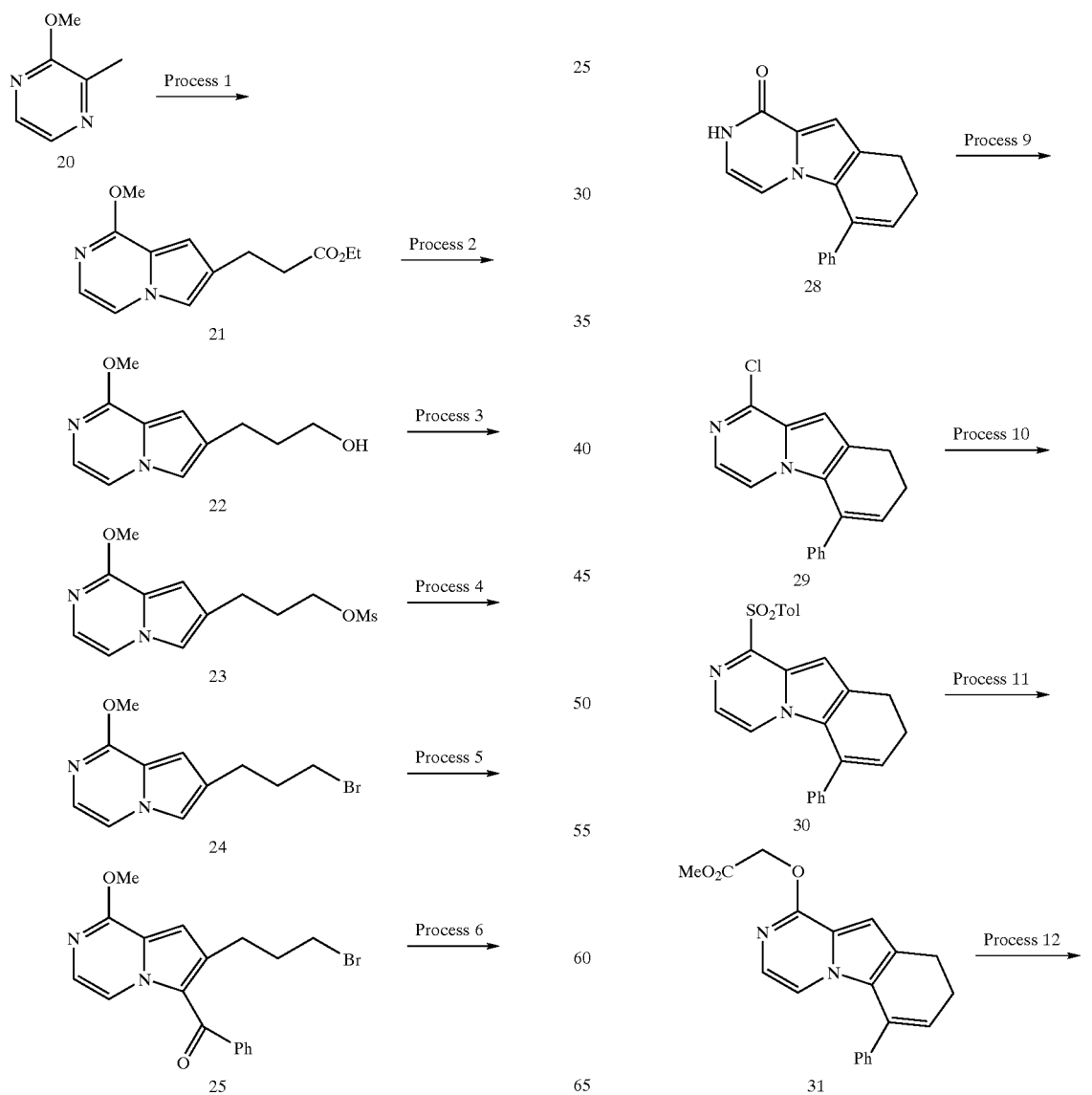

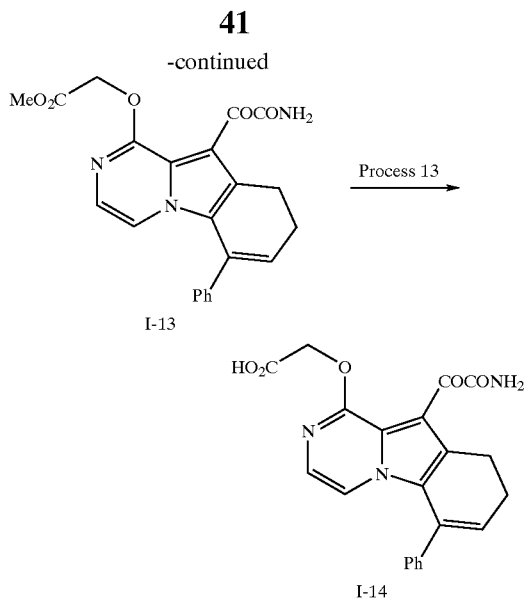

I-13

I-14

(Process 1)

The compound (21) was synthesized in a manner similar to that described in WO99/51605.

$^1$H-NMR (CDCl$_3$); δ 1.25 (3H, t, J=7.2 Hz), 2.65 (2, t, J=7.5 Hz), 2.99 (2H, t, J=7.5 Hz), 4.04 (3H, s), 4.14 (2H, q, J=7.2 Hz), 6.61 (1H, s), 7.03 (1H, d, J=4.8 Hz), 7.17 (1H, m), 7.40 (1H, dd, J=0.9, 4.8 Hz).

(Process 2)

To a solution of the compound (21) (5.22 g, 21.0 mmol) in ether (100 ml) was added gradually a suspension of lithium aluminum hydride (1.0 g, 26.3 mmol) in ether (20 ml) and the reaction mixture was stirred at room temperature for 2 h. After the reaction was completed, ice water was added thereto. The resulting mixture was stirred at room temperature for 1 h, and then the precipitated inorganic substance was filtrate and washed with tetrahydrofuran. The solvent was evaporated and the compound (22) (4.05 g, 93.4%) was given as light yellow oil.

$^1$H-NMR (CDCl$_3$); 1.41 (1H, brs), 1.87 –1.98 (2H, m), 2.76 (2H, t, J=7.5 Hz), 3.70 (2H, t, J=6.3 Hz), 4.04 (3H, s), 6.62 (1H, s), 7.03 (1H, d, J=4.8 Hz), 7.17 (1H, m), 7.41 (1H, dd, J=0.6, 4.8 Hz).

(Process 3)

To a solution of the compound (22) (4.36 g, 21.1 mmol) in dichloromethane (80 ml) were added triethylamine (3.12 ml, 22.4 mmol), and methanesulfonyl chloride (1.74 ml, 22.4 mmol) at −35° C. and the reaction mixture was stirred for 30 min in the same condition. The reaction mixture was poured into ice water, and to the mixture was added 1N hydrochloric acid 24 ml, and the resulting mixture was extracted with dichloromethane. The organic layer was washed with water and saturated sodium hydrogencarbonate solution, dried over magnesium sulfate and evaporated to give the compound (23) (6.01 g, 100%) as yellow oil. The product was used in the next process without purification.

(Process 4)

To a solution of the compound (23) (6.01 g, 21.1 mmol) in dimethylformamide (80 ml) was added lithium bromide (3.54 g, 40.8 mmol), then the mixture was stirred at 50° C. for 3 h. The reaction mixture was poured into ice water, and the resulting mixture was extracted with ethyl acetate. The organic layer was washed with saturated brine, dried over magnesium sulfate and evaporated. The residue was purified with silica gel chromatography (hexane:ethyl acetate=5:1), and the compound (24) (4.96 g, 87.2%) was given as yellow oil.

$^1$H-NMR (CDCl$_3$); 2.18 (2H, m), 2.83 (2H, t, J=7.5 Hz), 3.42 (2H, t, J=6.6 Hz), 4.04 (3H, s), 6.61 (1H, s), 7.04 (1H, d, J=4.5 Hz), 7.18 (1H, m), 7.41 (1H, dd, J=0.9, 4.5 Hz).

(Process 5)

To a solution of titanium tetrachloride (7.25 ml, 66.1 mmol) in nitromethane (50 ml) was added benzoyl chloride (7.68 ml, 66.2 mmol) at −20° C. and the mixture was stirred at 0° C. for 15 min, and then cooled at −20° C. again. To the mixture was added a solution of the compound (24) (5.93 g, 22.0 mmol) in nitromethane (20 ml), the resulting reaction mixture was stirred 0° C. for 1 h and then at room temperature for 1 h. The reaction mixture was poured into ice water, and the mixture was extracted with ethyl acetate. The organic layer was washed with aqueous ammonia and saturated brine, dried over magnesium sulfate and evaporated. The residue was purified with silica gel chromatography (hexane:ethyl acetate=9:1), and the compound (25) (2.55 g, 31.0%) was given as white powder.

$^1$H-NMR (CDCl$_3$); 1.98 (2H, m), 2.52 (2H, t, J=7.5 Hz), 3.15 (2H, t, J=6.6 Hz), 4.10 (3H, s), 6.31 (1H, d, J=5.1 Hz), 6.70 (1H, s), 7.45–7.53 (2H, m), 7.59 (1H, m), 7.76–7.71 (2H, m), 8.58 (1H, dd, J=0.9, 5.1 Hz).

(Process 6)

To a solution of the compouned (25) (2.53 g, 6.78 mmol) in acetonitrile (50 ml) was added triphenylphosphine (2.66 g, 10.1 mmol), then the reaction mixture was refluxed for 17 h and evaporated. To the residue was added ethyl acetate and ether, then the precipitate was filtrated to give phosphonium salt (26) (4.68 g) as yellow powder. The product was used in further reaction without purification.

(Process 7)

To a solution of the phosphonium salt (26) (4.68 g) obtained in Process 6 in acetonitrile 94 ml was added DBU (2.92 ml, 19.5 mmol) and the mixture was stirred at 60° C. for 3 h. After the reaction was completed, it was poured into ice water, acidified with 1N hydrochloric acid, and extracted with ethyl acetate. The organic layer was washed with a saturated brine, dried over magnesium sulfate and evaporated. The obtained residue was purified with the silica gel column chromatography (toluene:ethyl acetate=19:1) and the compound (27) (1.50 g, 80.1%) was obtained as light brown (yield 46.4%).

$^1$H-NMR (CDCl$_3$); 2.41–2.51 (2H, m), 2.87 (2H, t, J=7.8 Hz), 4.03 (3H, s), 5.92 (1H, t, J=4.8 Hz), 6.60 (1H, dd, J=0.9, 4.8 Hz), 6.72 (1H, d, J=0.9 Hz), 6.78 (1H, d, J=4.8 Hz), 7.27–7.32 (2H, m), 7.36–7.45 (3H, m).

(Process 8, 9)

The compound (29) was synthesized in a manner similar to that described in WO99/51605.

$^1$H-NMR (CDCl$_3$); 2.45–2.55 (2H, m), 2.93 (2H, t, J=8.1 Hz), 6.02 (1H, t, J=4.8 Hz), 6.81 (1H, dd, J=0.9, 4.8 Hz), 6.86 (1H, d, J=0.9 Hz), 7.00 (1H, d, J=4.8 Hz), 7.24–7.33 (2H, m), 7.37–7.47 (3H, m).

(Process 10)

The compound (30) was synthesized in a manner similar to that described in WO99/51605.

$^1$H-NMR (CDCl$_3$); 2.41 (3H, s), 2.47–2.56 (2H, m), 3.00 (2H, t, J=7.8 Hz), 6.08 (1H, t, J=4.8 Hz), 6.89 (1H, dd, J=0.9, 4.8 Hz), 7.18–7.29 (3H, m), 7.32 (2H, d, J=7.8 Hz), 7.37–7.44 (3H, m), 7.54 (1H, s), 8.00 (2H, d, J=7.8 Hz).

(Process 11)

The compound (31) was synthesized in a manner similar to that described in WO99/51605.

$^1$H-NMR (CDCl$_3$); 2.47–2.51 (2H, m), 2.88 (2H, t, J=7.8 Hz), 3.77 (3H, s), 4.99 (2H, s), 5.93 (1H, t, J=4.8 Hz), 6.61 (1H, d, J=0.9, 5.1 Hz), 6.72 (1H, d, J=5.1 Hz), 6.81 (1H, d, J=0.9 Hz), 7.25–7.32 (2H, m), 7.38–7.45 (3H, m).

(Process 12)

The compound (I-13) was synthesized in a manner similar to that described in WO99/51605.

$^1$H-NMR (CDCl$_3$); 2.45–2.55 (2H, m), 2.98–3.07 (2H, m), 3.75 (3H, s), 4.97 (2H, s), 5.62 (1H, br.s), 6.03 (1H, t, J=4.8 Hz), 6.68 (1H, br.s), 6.73 (1H, d, J=4.8 Hz), 6.94 (1H, d, J=4.8 Hz), 7.25–7.32 (2H, m), 7.38–7.45 (3H, m).

(Process 13)

The compound (I-14) was synthesized in a manner similar to that described in WO99/51605.

$^1$H-NMR (d$_6$-DMSO); 2.41–2.53 (2H, m), 2.88–2.97 (2H, m), 4.82 (2H, s), 6.10 (1H, t, J=4.8 Hz), 6.69 (1H, d, J=4.8 Hz), 7.10 (1H, d, J=4.8 Hz), 7.28–7.36 (2H, m), 7.42–7.52 (3H, m), 7.59 (1H, br.s), 7.98 (1H, br.s), 12.94 (1H, br.s).

Test Example

Inhibition Test of Human Secretory Phospholipase A$_2$ Analytical Experiment

In order to identify and evaluate an inhibitor of recombinant human secretory phospholipase A$_2$, the following chromogenic assay is utilized. The assay herein has been applied for high volume screening wherein 96 well microtiterplate is used. A general explanation for such assay is described in "Analysis of Human Synovial Fluid Phospholipase A$_2$ on Short Chain Phosphatidylcholine-Mixed Micelles: Development of a Spectrophotometric Assay Suitable for a Microtiterplate Reader" (Analytical Biochemistry, 204, pp 190–197, 1992 by Laure. J. Reynolds. Lori L. Hughes and Edward A. Dennis: the disclosure of which is incorporated herein for reference.

Reagents:
Reaction Buffer
  CaCl$_2$.6H$_2$O (2.19 g/L)
  KCl (7.455 g/L)
  Bovine Serum Albumin (fatty acid free) (1 g/L) (Sigma A-7030)
  Tris-HCl (3.94 g/L)
  pH 7.5 (adjusted with NaOH)
Enzyme Buffer
  0.05 M-AcONa
  0.2 M-NaCl
  pH 4.5 (adjusted with acetic acid)
DTNB
  198 mg of 5,5'-dithiobis-2-benzoic acid (manufactured by Wako Pure Chemicals) is dissolved in 100 ml of H$_2$O
  pH 7.5 (adjusted with NaOH)
Substrate Solution
  100 mg of racemic 1,2-bis(heptanoylthio)-1,2-dideoxy-sn-glyccro-3-phospholylcholine is dissolved in 1 ml of chloroform.
Triton-X 100
  624.9 mg of Triton-X 100 is dissolved in the reaction buffer.
Enzyme Solution
  Type I enzyme: sPLA$_2$ solution (330 ng/µl) (described in A. Kanda et. al., Biochimica et Biophysica Acta. 1171 (1992) 1–10) is dissolved in the assay (enzyme solution 27 µl is diluted with 1973 µl of the reaction buffer).
  Type II enzyme: 1 mg of sPLA$_2$ is dissolved in 1 ml of an enzyme buffer. Thereafter, the solution is maintained at 4° C. In the assay, 5 µl of the solution is diluted with 1995 µl of the reaction buffer to be used.
  Type V and Type X enzymes: cDNA sequences encoding human type V and Type X sPLA2 (Chen et., al., J. Biol. Chem., 1994. 269, 2365–2368 and Cupillard et., al., J. Biol. Chem., 1997, 272, 15745–15752) were inserted into downstream of promoter of pSVL SV40 Late Promoter Expression Vector (Amersham Pharmacia Biotech K. K.), mammalian cell expression vector, forwardly. The recombinant expression vectors were transfected into CHO host cells by LipofectAMINE regent (Invitrogen Japan K. K.) according to the attached manual and the cells expressed each of human type V and type X sPLA2 stably. After each expressing cells were cultured in α-MEM medium including 10% fetal serum albumin for 3 days, the cells supernatant were collected and measured enzymatic activity.

Enzyme Reaction: for 1 Plate of Microtiterplate 1) 0.106 ml of the substrate solution is put in a centrifugal tube, and nitrogen gas is jetted to remove the solvent. 0.54 ml of Triton-X 100 is added thereto, the mixture is stirred, thereafter it is sonified in a bath type sonification to dissolve. To the resulting product are added 17.8 ml of the reaction buffer and 0.46 ml of DTNB, and 0.18 ml each of the admixture is poured to wells of the 96 well microtiterplate.

2) 10 µl of a test compound (or solvent blank) are added in accordance with alignment of plates which has been previously set.

3) Incubation is effected at 40° C. for 15 minutes.

4) 90 ng/well in case of human type I enzyme, 50 ng/well in case of human type II enzyme, 40 µl/well in case of human type V enzyme, 15 µl/well in case of human type X enzyme were reacted.

5) Changes in absorbancy for 30 minutes for humane type I, type II, and type X enzyme and for 45 min for human type V enzyme, are measured by a plate reader, and inhibition activity was calculated (OD: 405 nm).

6) IC$_{50}$ was determined by plotting log concentration with respect to inhibition values within 10% to 90% inhibiting range.

Inhibitory activity of type II sPLA$_2$ is shown in table 1.

TABLE 1

| Compound No. | IC$_{50}$ (µM) |
|---|---|
| I-1 | 0.789 |
| I-2 | 0.045 |
| I-3 | 1.59 |
| I-4 | 0.054 |
| I-6 | 4.57 |
| I-8 | 0.262 |
| I-11 | 5.68 |
| I-12 | 0.178 |
| I-14 | 0.034 |

IC$_{50}$ value of the compound (14) is 0.097 µM for type I, 0.015 µM for type V, 0.022 µM for type X, respectively.

Formulation Example

It is to be noted that the following Formulation Examples 1 to 8 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

|  | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

|  | Dose (mg/capsule) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
| --- | --- |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| Active ingredient | 80 mg |
| --- | --- |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |

| | |
|---|---|
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| | |
|---|---|
| Active ingredient | 127 mg |
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

Industrial Applicability

The compounds according to the present invention have sPLA$_2$ inhibiting activity, so that the compounds of the invention inhibits sPLA$_2$-mediated fatty acid (such as arachidonic acid) release, whereby it is effective for treating septic shock and the like.

What is claimed is:

1. A compound represented by the formula (I):

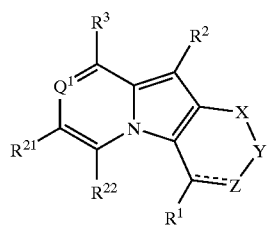

(I)

wherein $R^1$ is (a) C1 to C20 alkyl, C2 to C20 alkenyl, C2 to C20 alkynyl, carbocyclic groups, and heterocyclic groups, (b) the groups represented by (a) each substituted independently with at least one group selected from non-interfering substituents, or (c) —(CH$_2$)$_m$—R$_5$ wherein m is an integer from 1 to 6, and $R^5$ is a group selected from the groups (a) and (b);

$R^2$ is a group represented by the formula:

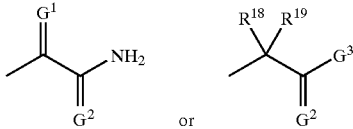

wherein $R^{18}$ and $R^{19}$ are independently a hydrogen atom, C1 to C3 alkyl or a halogen; $G^1$ and $G^2$ are independently an oxygen atom or a sulfur atom; and $G^3$ is —NH$_2$ or —NHNH$_2$;

$Q^1$ is a nitrogen atom or C—$R^4$;

one of $R^3$ and $R^4$ is —(L$^2$)-(acidic group) wherein L$^2$ is represented by the formula:

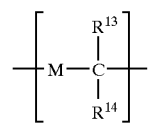

wherein M is —CH$_2$—, —O—, —N(R$^{15}$)—, or —S—; $R^{13}$ and $R^{14}$ are independently a hydrogen atom, C1 to C10 alkyl, aryl, aralkyl, carboxy, or a halogen, and $R^{15}$ is C1 to C6 alkyl; and the acidic group is represented by the formula:

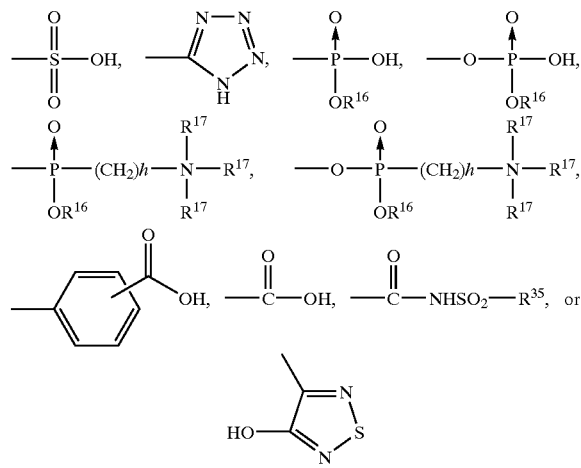

wherein $R^{16}$ is hydrogen atom, a metal, or C1 to C10 alkyl; $R^{17}$ is independently a hydrogen atom or C1 to C10 alkyl; $R^{35}$ is C1–C5 alkyl or phenyl; h is an integer from 1 to 8; and the other is a hydrogen atom, provided that when $Q^1$ is nitrogen, $R^3$ is —(L$^2$)-(acidic group) wherein L$^2$ and acidic group are as defined above;

$R^{21}$ and $R^{22}$ are independently a hydrogen atom, C1 to C6 alkyl, aryl, a halogen or aralkyl;

X is —CR$^{23}$R$^{24}$—, O, or S, wherein $R^{23}$ and $R^{24}$ are independently a hydrogen atom or C1 to C6 alkyl;

Y is a bond or —CR$^{25}$R$^{26}$—, wherein $R^{25}$ and $R^{26}$ are independently a hydrogen atom or C1 to C6 alkyl;

Z is CHR$^A$, CR$^A$, N, or NR$^B$, wherein $R^A$ is a hydrogen atom, alkyloxycarbonyl, or carboxy; $R^B$ is a hydrogen atom or acyl;

a broken line ( - - - ) represents the presence or absence of a bond, its prodrug, pharmaceutically acceptable salt, or solvate thereof.

2. A compound represented by the formula (II):

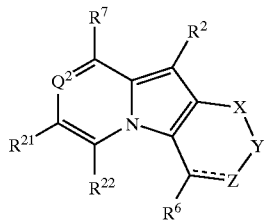
(II)

wherein $R^2$, $R^{21}$, $R^{22}$, X, Y, Z, and - - - are as defined in claim 1;

$R^6$ is —$(CH_2)_m$—$R^9$ wherein m is an integer from 0 to 6, and $R^9$ is (d) a group represented by the formula:

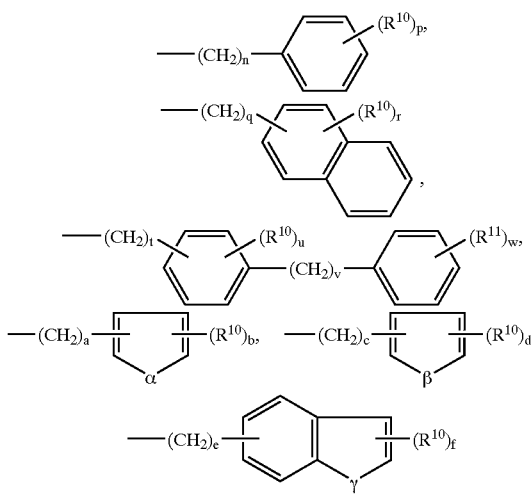

wherein a, c, e, n, q, t and v are independently an integer from 0 to 2; $R^{10}$ and $R^{11}$ are independently selected from a halogen, C1 to C10 alkyl, C1 to C10 alkyloxy, C1 to C10 alkylthio, optionally substituted phenyl, and C1 to C10 haloalkyl; α is an oxygen atom or a sulfur atom; β is —$CH_2$— or —$(CH_2)_2$—; γ is an oxygen atom or a sulfur atom; b is an integer from 0 to 3, d is an integer from 0 to 5; f, p, and w are independently an integer from 0 to 5; r is an integer from 0 to 7; and u is an integer from 0 to 4, or $R^9$ is (e) a member of (d) substituted with at least one substituent selected from the group consisting of C1 to C6 alkyl, C1 to C6 alkyloxy, C1 to C6 haloalkyloxy, C1 to C6 haloalkyl, phenyl, and a halogen;

$Q^2$ is a nitrogen atom or C—$R^8$;

one of $R^7$ and $R^8$ is —$(L^3)$—$R^{12}$ wherein $L^3$ is represented by the formula:

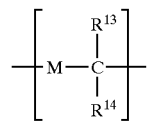

wherein M is —$CH_2$—, —O—, —$N(R^{15})$—, or —S—; $R^{13}$ and $R^{14}$ are independently a hydrogen atom, C1 to C10 alkyl, aryl, aralkyl, carboxy, or a halogen, and $R^{15}$ is C1 to C6 alkyl; and $R^{12}$ is represented by the formula:

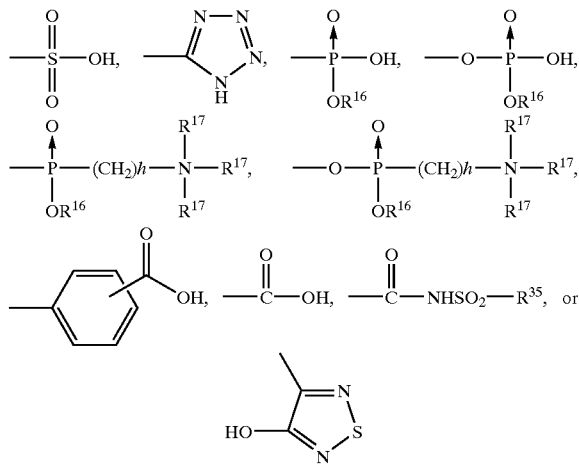

wherein $R^{16}$ is hydrogen atom, a metal, or C1 to C10 alkyl; $R^{17}$ is independently a hydrogen atom or C1 to C10 alkyl; $R^{35}$ is C1–C5 alkyl or phenyl; h is an integer from 1 to 8;

and the other is a hydrogen atom, its prodrug, pharmaceutically acceptable salt, or solvate thereof.

3. A compound, its prodrug, pharmaceutically acceptable salt, or solvate thereof as claimed in claim 1, wherein said $R^1$ is represented by the formula:

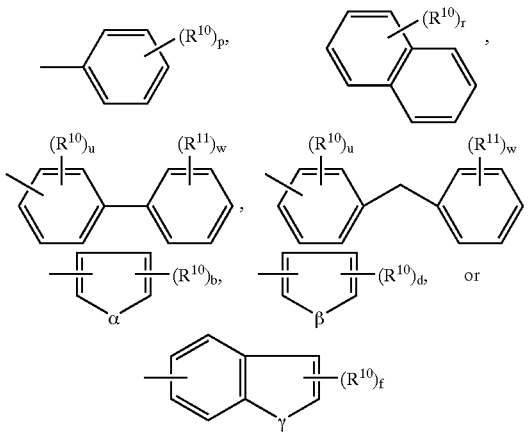

wherein $R^{10}$ and $R^{11}$ are independently selected from a halogen, C1 to C10 alkyl, C1 to C10 alkyloxy, C1 to C10 alkylthio, optionally substituted phenyl, and C1 to C10 haloalkyl; α is an oxygen atom or a sulfur atom; β is —CH$_2$— or —(CH$_2$)$_2$—; γ is an oxygen atom or a sulfur atom; b is an integer from 0 to 3, d is an integer from 0 to 5; f, p, and w are independently an integer from 0 to 5; r is an integer from 0 to 7; and u is an integer from 0 to 4.

4. A compound, its prodrug, pharmaceutically acceptable salt, or solvate thereof as claimed in claim 1, wherein said $R^1$ is represented by the formula:

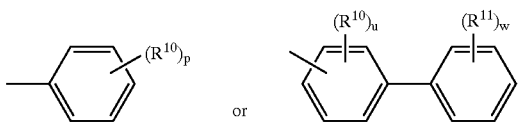

wherein $R^{10}$ and $R^{11}$ are independently selected from a halogen, C1 to C10 alkyl, C1 to C10 alkyloxy, C1 to C10 alkylthio, optionally substituted phenyl, and C1 to C10 haloalkyl; p and w are independently an integer from 0 to 5; and u is an integer from 0 to 4.

5. A compound, its prodrug, pharmaceutically acceptable salt, or solvate thereof as claimed in any claim 1, wherein said $R^3$ and $R^7$ are —O—(CH$_2$)$_g$—COOH (g is an integer from 1 to 6).

6. A compound, its prodrug, pharmaceutically acceptable salt, or solvate thereof as claimed in claim 1, wherein said $R^2$ is —COCONH$_2$.

7. A compound, its prodrug, pharmaceutically acceptable salt, or solvate thereof as claimed in claim 1, wherein said both $R^{21}$ and $R^{22}$ are hydrogen atoms.

8. A compound represented by the formula (III):

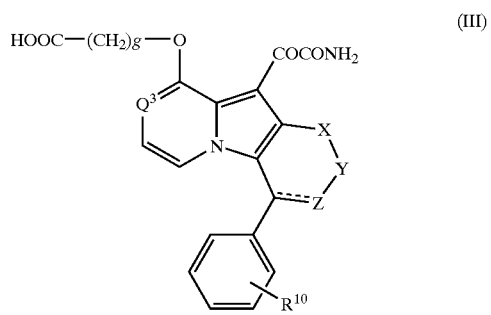

wherein $R^{10}$ is selected from a halogen, C1 to C10 alkyl, C1 to C10 alkyloxy, C1 to C10 alkylthio, optionally substituted phenyl, and C1 to C10 haloalkyl;
X is —CR$^{23}$R$^{24}$—, O, or S, wherein $R^{23}$ and $R^{24}$ are independently a hydrogen atom or C1 to C6 alkyl;
Y is a bond or —CR$^{25}$R$^{26}$—, wherein $R^{25}$ and $R^{26}$ are independently a hydrogen atom or C1 to C6 alkyl;
Z is CHR$^A$, CR$^A$, N, or NR$^B$, wherein $R^A$ is a hydrogen atom, alkyloxycarbonyl, or carboxy; $R^B$ is a hydrogen atom or acyl;
g is an integer from 1 to 6;
a broken line ( - - - ) represents the presence or absence of a bond;
$Q^3$ is a nitrogen atom, or CH,
its prodrug, pharmaceutically acceptable salt, or solvate thereof.

9. A compound, its prodrug, pharmaceutically acceptable salt, or solvate thereof as claimed in claim 1, wherein said (X, Y, Z) is (CH$_2$, CH$_2$, CH), (CH$_2$, CH$_2$, CH$_2$), (CH$_2$, CH$_2$, NR$^B$), (S, single bond, CR$^A$), or (S, single bond, CH), wherein $R^A$ and $R^B$ are as defined above.

10. A pharmaceutical composition containing comprising a compound as claimed in claim 1 and a pharmaceutically acceptable carrier.

11. A pharmaceutical composition as claimed in claim 10, which is for inhibiting sPLA$_2$.

12. A method for inhibiting sPLA$_2$, which comprises administration to a mammal of a compound as claimed in claim 1 in a parametrically effective amount.

* * * * *